(12) United States Patent
Barroso et al.

(10) Patent No.: US 11,793,761 B2
(45) Date of Patent: Oct. 24, 2023

(54) SOFT GEL CAPSULE PREPARATIONS

(71) Applicant: BAYER CONSUMER CARE AG, Basel (CH)

(72) Inventors: Aude Barroso, Darmstadt (DE); Maria Elena Iglesias, Alcala de Henares (ES); Maria Del Pilar Sanz Saiz, Madrid (ES); Blanca Alvarez Maluenda, Madrid (ES); Alberto Prior, Colmenar Viejo (ES); Javier Zumeta, Alcala de Henares (ES)

(73) Assignee: BAYER CONSUMER CARE AG, Basel (CH)

( * ) Notice: Subject to any disclaimer, the term of this patent is extended or adjusted under 35 U.S.C. 154(b) by 0 days.

(21) Appl. No.: 18/122,812

(22) Filed: Mar. 17, 2023

(65) Prior Publication Data
US 2023/0263738 A1    Aug. 24, 2023

Related U.S. Application Data

(62) Division of application No. 18/055,880, filed on Nov. 16, 2022.

(30) Foreign Application Priority Data

Feb. 24, 2022    (EP) .................................. 22382160

(51) Int. Cl.
| A61K 9/48 | (2006.01) |
| A61K 36/185 | (2006.01) |
| A61K 47/36 | (2006.01) |
| A61K 47/02 | (2006.01) |
| A61K 47/44 | (2017.01) |
| A61K 36/534 | (2006.01) |
| A61K 36/28 | (2006.01) |
| A61K 36/53 | (2006.01) |
| A61K 36/23 | (2006.01) |
| A61K 36/484 | (2006.01) |
| A61K 36/31 | (2006.01) |

(52) U.S. Cl.
CPC ............ *A61K 9/4825* (2013.01); *A61K 9/485* (2013.01); *A61K 9/4816* (2013.01); *A61K 9/4858* (2013.01); *A61K 9/4866* (2013.01); *A61K 9/4875* (2013.01); *A61K 36/185* (2013.01); *A61K 36/23* (2013.01); *A61K 36/28* (2013.01); *A61K 36/31* (2013.01); *A61K 36/484* (2013.01); *A61K 36/53* (2013.01); *A61K 36/534* (2013.01); *A61K 47/02* (2013.01); *A61K 47/36* (2013.01); *A61K 47/44* (2013.01)

(58) Field of Classification Search
CPC .... A61K 9/4825; A61K 36/185; A61K 47/36; A61K 47/02; A61K 47/44; A61K 36/534; A61K 9/4875; A61K 36/28; A61K 8/485; A61K 36/53; A61K 36/23; A61K 36/484; A61K 9/4816; A61K 9/4858
See application file for complete search history.

(56) References Cited

U.S. PATENT DOCUMENTS

| 9,434,986 B2 | 9/2016 | Liu et al. |
| 9,435,007 B2 | 9/2016 | Han et al. |
| 9,435,028 B2 | 9/2016 | Dickey |
| 2009/0041866 A1 * | 2/2009 | Miyata ................. A61K 31/357 514/23 |
| 2021/0137917 A1 | 5/2021 | Teli et al. |

FOREIGN PATENT DOCUMENTS

| CN | 103751799 A | 4/2014 |
| WO | 2009100970 A1 | 8/2009 |

OTHER PUBLICATIONS

Ebert; Wr, "Soft elastic gelatin capsules: a unique dosage form", Pharmaceutical Technology, 1977, vol. 1 No 5, 44-50.
Gullapalli; Rampurna, "Soft Gelatin Capsules (Softgels)", Journal of Pharmaceutical Sciences, 2010, vol. 99 No. 10, 4107-4148.
Jimerson Robert; et al, "Soft Gelatin Capsijle Update", Drug Development and Industry Pharmacy, 1986, vol. 12 No. 8 & 9, 1133-1144.
Kelber; et al, "Ex vivo/in vitro absorption of STW 5 (Iberogast (R)) and its extract components", Phytomedicine, 2006, vol. 13, 107-113.
Patel MS; et al, "Advances in softgel formulation technology", Manufacturing Chemist, Jul. 1989, vol. 60 No. 7, 26-28.
Patel MS; et al, "Softgel Technology", Manufacturing Chemist, Aug. 1989, vol. 60 No. 8, 47-49.

* cited by examiner

*Primary Examiner* — Shirley V Gembeh
(74) *Attorney, Agent, or Firm* — David Schramm; James Dilmore

(57) ABSTRACT

The disclosure relates to a pharmaceutical or dietary composition in the form of a soft gel capsule comprising a liquid or semisolid fill and a shell, the fill comprising at least one active ingredient or dietary supplement, dissolved, suspended or solubilized in a solution comprising water and alcohol, and a solubilizer and thickening agent. The disclosure furthermore relates to methods of reducing brittleness and fragility of such soft gel capsules.

16 Claims, No Drawings

SOFT GEL CAPSULE PREPARATIONS

CROSS-REFERENCE TO RELATED APPLICATIONS

The present application is a Divisional Application of U.S. application Ser. No. 18/055,880, filed Nov. 16, 2022, which is a U.S. National application filing under 35 U.S.C. § 111(a), and claims the benefit of EP application number 22382160.4, filed Feb. 24, 2022, the disclosures of which are hereby incorporated by reference in their entirety.

TECHNICAL FIELD

The disclosure relates to a pharmaceutical or dietary composition in the form of a soft gel capsule comprising a liquid or semisolid fill and a shell, the fill comprising at least one active ingredient or dietary supplement, dissolved, suspended or solubilized in a solution comprising water and alcohol, and a solubilizer and thickening agent. The disclosure furthermore relates to methods of reducing brittleness and fragility of such soft gel capsules.

BACKGROUND OF THE DISCLOSURE

The use of softgel capsules is increasing across a wide range of applications including prescription medicines, consumer health, vitamins, and mineral supplements.

The method for manufacturing a softgel product occurs in five stages: preparation of the shell mass, manufacturing of fill material, encapsulation process, drying, and finishing (see, e.g., Hutchison K G, Ferdinando J. "Soft capsules". In: Aulton M E, Taylor K M G. Aulton's pharmaceutics: the design and manufacture of medicine. Elsevier Health Sciences 2013, pp 597-610).

Traditionally, the outer shell (the "shell") is prepared from gelatin, plasticizer(s) and water. Optional materials could be included into the shell formula such as opacifiers, colorants, flavors, sweeteners and preservatives. This material is shaped into the shell that forms the outermost layer of the capsule and holds the fill material, which typically contains the active ingredient(s) or nutrient(s) and the excipient(s) that are used to fill the shell itself (the "fill").

One of the common challenges associated with soft gel capsule performance is the tendency of the capsules to be brittle, especially soft gel capsules containing a hygroscopic fill are challenging. Capsule manufacturers often associate poor performance of such a capsule to manufacturing processes or storage conditions. However, the composition of the shell and/or fill formulation also play an important role in this phenomenon.

Preventing brittleness can on the one hand be related to maintaining the optimal malleability in the capsule shell, although other factors, such as filling pressure and impacts during packaging, storing and/or transporting processes, also play a role.

The elasticity and malleability of the shell material is also related to the moisture content of the capsule shell. In this sense and in a constant manner, the water of the shell formula migrates from the shell material to the environment. Softgels newly formed at the encapsulating machine show a moisture content between about 35-40% (weight by weight; w/w). During the drying process, the air penetrates the shell moving the water outward to the softgel surface reducing the initial water content to about 20-25% (w/w) in the first or dynamic drying process and to about 10-15% (w/w) in the second or static drying process (see, e.g., Gullapalli R P. Soft gelatin capsules (softgels). J Pharm Sci. 2010; 99(10): 4107-48), wherein if the capsules lose an excessive amount of moisture (over-dried) they tend to become brittle. This phenomenon also takes place during storage. In order to minimize water migration, factors such as the gelatin age, gelatin ribbon thickness and the lubricant used during the encapsulation process can be optimized, and the drying and storing conditions (temperature, humidity and air flow conditions) can be further controlled.

Moreover, the free water and glycerol of the shell formula can migrate to the fill. The presence of hygroscopic compounds in the filling, which attract water from its surroundings through either absorption or adsorption, can promote brittle capsules by decreasing the elasticity of the shell material or increasing internal pressure.

In addition, migration also occurs in the other direction from the fill into the shell, which is a special problem encountered when the fill contains a high amount of water and/or alcohol, as is the case for plant extracts that usually contain a substantial amount of alcohol and water to keep the extracted compounds soluble in the fill. As described for the water migration from shell to fill, also the migration from the fill into the shell leads to brittleness of the capsules as well as misshaping of the capsules and fragility.

The proper design for a specific soft gel capsule formulation therefore requires the appropriate selection of shell and fill composition and specifically the optimization of the fill composition to allow for the efficient production of a chemically and physically stable product with the desired biopharmaceutical properties.

Consequently, it is important to realize that the formulation composition itself are important for the overall capsule performance, including its tendency to become brittle. Extensive experience in the field of soft gel capsule manufacturing is thus needed to develop capsules that are suitable for specific active ingredients and dietary supplements.

The present disclosure therefore confronts the technical problem of providing fill and shell combinations for soft gel capsules that are suitable for encapsulating active ingredients or dietary supplements having a hygroscopic and/or hydrophilic fill composition and that can overcome the above-mentioned problems of brittleness and fragility of such soft gel capsules.

SUMMARY

The present disclosure therefore relates to a pharmaceutical or dietary supplement composition in the form of a soft gel capsule, the capsule comprising a liquid or semisolid fill and a shell,
wherein the fill comprises
  a) at least one active ingredient or dietary supplement dissolved, suspended or solubilized in a solution comprising less than 50% (w/w) of water and less than 5% (w/w) of alcohol, preferably ethanol
  b) at least one solubilizer, wherein the solubilizer is selected from low molecular weight polyethylene glycol (PEG), preferably PEG with a molecular weight of 300 to 600, such as Macrogol 400, or Macrogol 600, plant oils such as soybean oil, sunflower oil, olive oil and maize oil and medium-chain triglycerides, preferably wherein the solubilizer is Macrogol 600, sunflower oil, olive oil or maize oil; and
  c) at least one thickening agent, wherein the thickening agent is selected from high molecular weight polyethylene glycol, preferably Macrogol 4000, beeswax, Geleol™ mono and diglycerides NF, such as Glycerol monostearate 40-55 (Type I) EP/Mono, colloidal silicone dioxide, hard fat, Lauroyl polyoxylglycerides, such as Gelucire® 44/14, or Stearoyl macrogol glycerides, such as Gelucire® 50/13, or combinations thereof; and wherein the shell comprises an edible polymer and/or plasticizer, and optionally an opacifier and/or colorants.

In a further embodiment of the present disclosure the solution comprising water and alcohol comprises
i. less than 5% (w/w), or less than 4% (w/w), or less than 3% (w/w), or less than 2%, or less than 1% (w/w), or less than 0.5% (w/w), or less than 0.25% (w/w) of alcohol, preferably ethanol, and
ii. less than 50% (w/w), or less than 45% (w/w), or less than 40% (w/w), or less than 35% (w/w), or less than 30% (w/w), or less than 25% (w/w), or less than 20% (w/w), or less than 15% (w/w) of water.

In one embodiment of present disclosure the solution comprising water and alcohol comprises
i. between 5% to 0.2% (w/w), or between 4% to 0.5% (w/w), or between 3% to 1% (w/w), or between 2% to 1% (w/w), or between 2% to 0.5% (w/w), or between 1% to 0.2% (w/w) of alcohol, preferably ethanol; and
ii. between 10% to 50% (w/w), between 20% to 50% (w/w), between 30% to 50% (w/w), between 35% to 50% (w/w), between 40% to 50% (w/w), between 45% to 50% (w/w), between 15% to 49% (w/w), between 20% to 48% (w/w), between 25% 15 to 47% (w/w), between 30% to 46% (w/w), between 35% to 45% (w/w) of water.

In one embodiment of the pharmaceutical or dietary supplement composition of present disclosure
a) the active ingredient is dissolved, suspended or solubilized in a solution comprising less than 2% (w/w) of ethanol and less than 50% (w/w) of water; and
b) the at least one solubilizer is selected from Macrogol 600, sunflower oil, olive oil and maize oil, or combinations thereof; and
c) the at least one thickening agent is selected from Macrogol 4000, Geleol™ Mono and Diglycerides NF, colloidal silicone dioxide and beeswax, or combinations thereof; and wherein the shell comprises an edible polymer and/or plasticizer, and optionally an opacifier and/or colorants.

In a further embodiment of the pharmaceutical or dietary supplement composition the active ingredient is a hydrophilic active ingredient, preferably a hydrophilic plant extract, more preferably a highly concentrated hydrophilic plant extract.

In one embodiment the active ingredient is a plant extract comprising at least one of Matricaria flower liquid extract, Peppermint leaves liquid extract, Liquorice root liquid extract, Caraway fruit liquid extract, Bitter candytuft fresh plant liquid extract, Melissa leaf liquid extract, Chamomile flowers liquid extract, Lemon balm leaf liquid extract, Angelica root liquid extract, Celandine herb liquid extract, Milk thistle fruit liquid extract, or combinations thereof.

In one embodiment the active ingredient is a plant extract comprising Matricaria flower liquid extract, Peppermint leaves liquid extract, Liquorice root liquid extract, Caraway fruit liquid extract, Bitter candytuft fresh plant liquid extract and Melissa leaf liquid extract. In a preferred embodiment the active ingredient is Iberogast N concentrate as further detailed in the description below.

In one embodiment the active ingredient is a plant extract comprising Chamomile flowers liquid extract, Peppermint leaves liquid extract, Liquorice root liquid extract, Caraway fruit liquid extract, Bitter candytuft fresh plant liquid extract, Lemon balm leaf liquid extract, Angelica root liquid extract, Celandine herb liquid extract and Milk thistle fruit liquid extract.

In one embodiment the active ingredient is a plant extract comprising at least one of American aspen or aspen stem bark and leaves liquid extract, Common ash stem bark liquid extract, European goldenrod herb liquid extract, or a combination thereof.

In one embodiment of present disclosure the edible polymer is selected from gelatine, gelatine RXL, gelatine GELITA® RXL R2 and non-animal derived compounds, such as Seagel® CAP 203, carrageenan, vegetable starch, such as for example maize or pea starch, or combinations thereof, preferably gelatine GELITA® RXL R2 or Seagel® CAP 203.

In a preferred embodiment of the pharmaceutical or dietary supplement composition of present disclosure
a) the active ingredient is Iberogast N concentrate,
b) the at least one solubilizer is selected from Macrogol 600, sunflower oil, olive oil and maize oil, or combinations thereof; and
c) the at least one thickening agent is selected from Macrogol 4000, Geleol™ Mono and Diglycerides NF, colloidal silicone dioxide and beeswax, or combinations thereof; and
d) wherein the shell comprises an edible polymer selected from gelatine, gelatine RXL, gelatine GELITA® RXL R2 and non-animal derived compounds, such as Seagel® CAP 203, carrageenan, vegetable starch, such as for example maize or pea starch, or combinations thereof, preferably gelatine GELITA® RXL R2 or Seagel® CAP 203.

In yet a further embodiment of present disclosure, the plasticizer is selected from glycerine, propylene glycol, mannitol, sorbitan, sorbitol, or similar low molecular weight polyols, or combinations thereof.

In one embodiment the opacifier is selected from starch, titanium dioxide, calcium carbonate, zinc oxide, tricalcium phosphate, iron oxides, or combinations thereof.

In one embodiment the colorants are selected from synthetic colorants or natural colorants.

In a further embodiment of the pharmaceutical or dietary supplement composition of present disclosure the water activity value of the fill is between 0.30 and 0.60, preferably between 0.35 and 0.50, more preferably between 0.37 and 0.47, most preferred between 0.38 and 0.45.

In a further embodiment of the pharmaceutical or dietary supplement composition of present disclosure the water activity value of the fill is between 0.70 and 0.90, preferably between 0.73 and 0.85, more preferably between 0.74 and 0.84, most preferred between 0.75 and 0.83.

The present disclosure furthermore relates to a method of reducing brittleness of a softgel capsule as described herein, wherein a solubilizer is added to the fill before encapsulation with the shell, wherein the solubilizer is selected from Macrogol 400, Macrogol 600, plant oils such as soybean oil, sunflower oil, olive oil and maize oil, preferably wherein the solubilizer is Macrogol 600, sunflower oil, olive oil or maize oil.

The present disclosure also relates to method of reducing the fragility of a softgel capsule as described herein, the method comprising a step of adding a solubilizer to the fill before encapsulation with the shell, wherein the solubilizer is selected from Macrogol 400, Macrogol 600, plant oils such as soybean oil, sunflower oil, olive oil and maize oil, preferably wherein the solubilizer is Macrogol 600, sunflower oil, olive oil or maize oil.

The present disclosure furthermore relates to a pharmaceutical or dietary supplement composition as described herein for use in the treatment of functional disorders of the gastrointestinal (GI) tract, such as functional dyspepsia (FD) and irritable bowel syndrome (IBS), minor gastro-intestinal complaints, such as bloating, minor spasms, a burning sensation, pain, inflammations, swelling and functional impairments accompanying diseases of the locomotor apparatus of rheumatic origin, such as rheumatoid arthritis, arthroses, spinal syndromes, epicondylitis, periarthritis, Bechterew's disease and/or lumbago.

DESCRIPTION OF THE DISCLOSURE

The present disclosure may be understood more readily by reference to the following detailed description of the preferred embodiments of the disclosure, and to the examples included therein.

The proper design for a specific soft gel capsule formulation requires the appropriate selection of shell and fill composition and the optimization of the two to allow for the efficient production of a chemically and physically stable product with the desired biopharmaceutical properties.

The present disclosure confronts the technical problem of providing fill and shell combinations for soft gel capsules that are suitable for encapsulating active ingredients or dietary supplements having a hygroscopic and/or hydrophilic fill composition and that can overcome the above-mentioned problems of brittleness and fragility of such soft gel capsules.

The present disclosure therefore relates to a pharmaceutical or dietary supplement composition in the form of a softgel capsule, the capsule comprising a liquid or semisolid fill and a shell,
wherein the fill comprises
  a) at least one active ingredient or dietary supplement dissolved, suspended or solubilized in a solution comprising less than 50% (w/w) of water and less than 5% (w/w) of alcohol, preferably ethanol
  b) at least one solubilizer, wherein the solubilizer is selected from low molecular weight polyethylene glycol (PEG), preferably PEG with a molecular weight of 300 to 600, such as Macrogol 400, or Macrogol 600, plant oils such as soybean oil, sunflower oil, olive oil and maize oil and medium-chain triglycerides, preferably wherein the solubilizer is Macrogol 600, sunflower oil, olive oil or maize oil; and
  c) at least one thickening agent, wherein the thickening agent is selected from high molecular weight polyethylene glycol, preferably Macrogol 4000, beeswax, Geleol mono and diglycerides, such as Glycerol monostearate 40-55 (Type I) EP/Mono, colloidal silicone dioxide, hard fat, Lauroyl polyoxylglycerides, such as Gelucire® 44/14, or Stearoyl macrogol glycerides, such as Gelucire® 50/13, or combinations thereof and
wherein the shell comprises an edible polymer and/or plasticizer, and optionally an opacifier and/or colorants.

As used herein, the term "pharmaceutical composition" means a composition, which is suitable for prescription and OTC medicaments, and which are available from doctors, in chemist's shop or in drugstores, only.

As used herein, the term "dietary supplement composition" means a composition, which is for supplementing the regular food intake with additional nutritional elements to enhance quality of life, and which are freely available without prescription in groceries or supermarket, but not only in drugstores.

The active ingredient or dietary supplement of present disclosure is solubilized, suspended or dissolved in a solution comprising water and alcohol, preferably ethanol. It is to be understood, that the active ingredients and dietary supplements of present disclosure require a hydrophilic environment which increases the problems when encapsulation in a soft gel capsule is desired. The active ingredient according to present disclosure can be any component that provides pharmacological activity or other direct effect in the treatment, or prevention of disease, or affects the structure or any function of the body.

In a further embodiment of the present disclosure the solution comprising water and alcohol comprises
  i. less than 5% (w/w), or less than 4% (w/w), or less than 3% (w/w), or less than 2%, or less than 1% (w/w), or less than 0.5% (w/w), or less than 0.25% (w/w) of alcohol, preferably ethanol, and
  ii. less than 50% (w/w), or less than 45% (w/w), or less than 40% (w/w), or less than 35% (w/w), or less than 30% (w/w), or less than 25% (w/w), or less than 20% (w/w), or less than 15% (w/w) of water.

In one embodiment of present disclosure the solution comprising water and alcohol comprises
  i. between 5% to 0.2% (w/w), or between 4% to 0.5% (w/w), or between 3% to 1% (w/w), or between 2% to 1% (w/w), or between 2% to 0.5% (w/w), or between 1% to 0.2% (w/w) of alcohol, preferably ethanol; and
  ii. between 10% to 50% (w/w), between 20% to 50% (w/w), between 30% to 50% (w/w), between 35% to 50% (w/w), between 40% to 50% (w/w), between 45% to 50% (w/w), between 15% to 49% (w/w), between 20% to 48% (w/w), between 25% to 47% (w/w), between 30% to 46% (w/w), between 35% to 45% (w/w) of water.

In one embodiment of the pharmaceutical or dietary supplement composition of present disclosure
  a) the active ingredient is dissolved, suspended or solubilized in a solution comprising less than 2% (w/w) of ethanol and less than 50% (w/w) of water; and
  b) the at least one solubilizer is selected from Macrogol 600, sunflower oil, olive oil and maize oil, or combinations thereof; and
  c) the at least one thickening agent is selected from Macrogol 4000, Geleol™ Mono and Diglycerides NF, colloidal silicone dioxide and beeswax, or combinations thereof; and
  wherein the shell comprises an edible polymer and/or plasticizer, and optionally an opacifier and/or colorants.

In a further embodiment of the pharmaceutical or dietary supplement composition the active ingredient is a hydrophilic active ingredient, preferably a hydrophilic plant extract, more preferably a highly concentrated hydrophilic plant extract.

In one embodiment the active ingredient is a plant extract comprising at least one of Matricaria flower liquid extract, Peppermint leaves liquid extract, Liquorice root liquid extract, Caraway fruit liquid extract, Bitter candytuft fresh plant liquid extract, Melissa leaf liquid extract, Chamomile flowers liquid extract, Lemon balm leaf liquid extract, Angelica root liquid extract, Celandine herb liquid extract, Milk thistle fruit liquid extract, or combinations thereof.

It is to be understood that the above listed plant extracts can be mixed in any combination using two, three, four, five, six, seven, eight, nine, ten, eleven or all twelve extracts for preparing a plant extract according to present disclosure.

In one embodiment the active ingredient is a plant extract comprising at least one of Chamomile flowers liquid extract, Peppermint leaves liquid extract, Liquorice root liquid extract, Caraway fruit liquid extract, Bitter candytuft fresh plant liquid extract, Lemon balm leaf liquid extract, Angelica root liquid extract, Celandine herb liquid extract, Milk thistle fruit liquid extract, or a combination thereof. It is to be understood that the listed plant extracts can be mixed in any combination using two, three, four, five, six, seven, eight, nine or ten of these extracts for preparing a plant extract according to present disclosure. Preferred is a combination comprising all ten extracts.

In one embodiment the active ingredient is a plant extract comprising Chamomile flowers liquid extract, Peppermint leaves liquid extract, Liquorice root liquid extract, Caraway fruit liquid extract, Bitter candytuft fresh plant liquid extract, Lemon balm leaf liquid extract, Angelica root liquid extract, Celandine herb liquid extract and Milk thistle fruit liquid extract.

In a further embodiment the active ingredient is a plant extract comprising at least one of American aspen or aspen stem bark and leaves liquid extract, Common ash stem bark liquid extract, European goldenrod herb liquid extract, or a combination thereof. It is to be understood that the plant extracts can be mixed in any combination using two or three of these extracts for preparing a plant extract according to present disclosure. Preferred is a combination of all three extracts.

In a preferred embodiment the active ingredient is a plant extract comprising Matricaria flower liquid extract, Peppermint leaves liquid extract, Liquorice root liquid extract, Caraway fruit liquid extract, Bitter candytuft fresh plant liquid extract and Melissa leaf liquid extract.

In preferred embodiment the active ingredient is Iberogast N concentrate.

As described in Example 2, Iberogast N concentrate is the product of the distillation process of Iberogast N to eliminate ethanol and reduce water content to obtain a feasible material to be encapsulated in a soft gel capsule. During the manufacturing process, the active ingredient Iberogast N is concentrated by distillation being the Iberogast N dosage of 1 ml transformed in around 78 to 82 µl of Iberogast N concentrate, which is the concentrated form of Iberogast N.

As used herein, Iberogast N refers to a plant extract comprising a combination of Matricaria flower liquid extract, Peppermint leaves liquid extract, Liquorice root liquid extract, Caraway fruit liquid extract, Bitter candytuft fresh plant liquid extract, Melissa leaf liquid extract as disclosed in Table 6 of Example 2.

As described above one of the main challenges associated with encapsulating hydrophilic and/or hygroscopic fill formulations is the tendency of migration of the water and alcohol from the fill into the shell. This can be seen in Example 1, where several attempts to encapsulate Iberogast®, a plant extract comprising a water content of about 68% (w/w) and an ethanol content of at least 29.5% (w/w), in soft gel capsules were made. As a result of this and in order to reduce the water and ethanol content of the plant extract to be filled into the soft gel capsules, Iberogast N concentrate was prepared as described above. One preferred embodiment of present disclosure is therefore a pharmaceutical or dietary supplement composition in which the fill comprises as the at least one active ingredient Iberogast N concentrate. As shown in Example 2 the reduction of the water and ethanol content did lead to better results, however, the soft gel capsules showed brittleness and fragility that compromised their stability during product handling and storage. The use of soya oil as a solubilizer and beeswax as a thickener to the fill resulted in more storage stable soft gel capsules that showed no sign of brittleness after 12 months of storage. These capsules, however, showed less flexibility after longer storage, as well as stickiness. Alternative formulations were therefore developed to overcome also these slight disadvantages, as shown in Examples 3 to 8.

Therefore, in order to further reduce the brittleness of the soft gel capsules comprising Iberogast N concentrate, at least one solubilizer selected from Macrogol 600, sunflower oil, olive oil and maize oil, or combinations thereof was added to the fill in combination with at least one thickening agent selected from Macrogol 4000, Geleol™ Mono and Diglycerides NF, colloidal silicone dioxide and beeswax, or combinations thereof.

Another issue that was observed during the development of such soft gel capsules was the misshapenness of the capsules depending on the fill composition chosen. As described herein the term "misshapenness" refers to the deformity of the capsules. These capsules are stickier to the packaging material, harder to swallow and detrimental to the quality perception of the consumer. Such misshapenness is therefore to be avoided.

The solubilizers according to present disclosure are selected from low molecular weight polyethylene glycol (PEG), preferably PEG with a molecular weight of 300 to 600, such as Macrogol 400, or Macrogol 600, plant oils such as soybean oil, sunflower oil, olive oil and maize oil and medium-chain triglycerides, preferably wherein the solubilizer is Macrogol 600, sunflower oil, olive oil or maize oil.

Polyethylene glycols, due to their ability to be miscible with aqueous fluids in all proportions can dissolve many pharmaceutical compounds while at the same time making them ideal vehicles for the delivery. Polyethylene Glycols with molecular weights in the range of 300 to 600 can be used as hydrophilic vehicles for fill formulations for soft gel capsules. The solubilization capacity of the polyethylene glycols is increased with the low molecular weight. However, the use is limited due to their ability to diffuse into the shell and thereby act as a plasticizer for gelatine or other shell material. The extent of diffusion of a polyethylene glycol from the film into the shell decreases with an increase in its molecular weight. As such Macrogol 600 is chosen as the most preferred solubilizer for fill development of present disclosure due to its lower hygroscopicity than other lower molecular weight PEGs, such as for example Macrogol 400.

Further preferred solubilizers of present disclosure are plant oils that upon addition to the fill composition can reduce the undesired fill-shell migration. Preferred plant oils are soybean oil, sunflower oil, olive oil and maize oil.

Soybean oil is a fatty oil extracted from the seeds of *Glycine max*. Sunflower oil is a fatty oil obtained from the seeds of *Helianthus annuus* by mechanical expression or by extraction which is then refined. Olive oil is a fatty oil obtained by refining of crude olive oil, obtained by cold expression or other suitable mechanical means from the ripe drupes of *Olea europaea*. Maize oil is a fatty oil obtained from the seeds of *Zea mays* by expression or by extraction which is then refined.

The thickening agents of present disclosure are added into the fill composition as emulsifying and viscosity increasing agents. The thickening agent of present disclosure is selected from high molecular weight polyethylene glycol, preferably Macrogol 4000, Geleol™ mono and diglycerides NF, preferably Glycerol monostearate 40-55 (Type I) EP/Mono, colloidal silicone dioxide, beeswax, hard fat, Lauroyl polyoxylglycerides, such as Gelucire® 44/14, or Stearoyl macrogol glycerides, such as Gelucire® 50/13, or combinations thereof.

Geleol™ mono and diglycerides NF (Glycerol monostearate 40-55 (Type I) EP/Mono and diglycerides NF) is a glyceride with an intermediate melting point used as a lipidic vehicle and modified release agent. In capsules it can be used as a modified release matrix former and a coating agent for taste masking or as a consistency agent.

The suitable thickening agents as well as the solubilizers are further described in the examples section.

In one embodiment of present disclosure the edible polymer is selected from gelatine, gelatine RXL, gelatine GELITA® RXL R2 and non-animal derived compounds, such as Seagel® CAP 203, carrageenan, vegetable starch, such as for example maize or pea starch, or combinations thereof, preferably gelatine GELITA® RXL R2 or Seagel® CAP 203.

As is common with liquid-based capsule formulations, the encapsulating material may be a soft outer shell. As such, the present disclosure provides for a soft gel capsule comprising an outer shell encapsulating the inner fill. Also provided are an outer shell and compositions and/or mixtures to be used in the preparation of the outer shell. As understood in the art, a typical outer shell for a soft gel capsule may contain gelatine or non-animal derived components as the principal encapsulating material, water, and plasticizers such as glycerine and/or sorbitol-sorbitan solution to allow the gelatine or the non-animal derived components to be formed to and retain the desired capsule shape. However, in addition to the gelatine and non-animal derived components, water, glycerine and/or sorbitol-sorbitan solution of a typical outer shell, the outer shells of present disclosure may contain one or more further colorants, such as pearlescent pigments or other opaque materials, making the soft gel capsule visually appealing to the consumer.

In one preferred embodiment of present disclosure the soft gel capsules comprise gelatine as the primary matrix for the outer shell, as the physical properties of the gelatine may be readily modified with plasticizers or colorants as needed. Certain grades of gelatine, as characterized by, for example, bloom strength, may be utilized in the outer shell.

In one embodiment, the shell of the capsules comprises from about 20% to about 60% (w/w) gelatine, more preferably from about 25% to about 52% (w/w) gelatine, and most preferably from about 40% to about 52% (w/w) gelatine. The gelatine can be of Type A or Type B, or a mixture thereof with bloom numbers ranging from about 60 to about 300, more preferred from about 100 to 180 bloom.

In some embodiments, the gelatine outer shell comprises at least about 35 wt %, at least about 40 wt %, at least about 41 wt %, at least about 42 wt %, at least about 43 wt %, at least about 44 wt %, at least about 45 wt %, at least about 46 wt %, at least about 47 wt %, at least about 48 wt %, at least about 49 wt %, at least about 50 wt %, at least about 51 wt %, at least about 52 wt %, at least about 53 wt % gelatine of the total weight of the shell.

In some embodiments, the shell comprises non-animal derived components, such as Seagel® CAP 203, carrageenan, vegetable starch, such as for example maize or pea starch, or combinations thereof, as the primary matrix for the outer shell. Its physical properties can be readily modified with plasticizers and/or colorants as needed.

In some embodiments, the outer shell comprising non-animal derived components comprises at least about 20 wt %, at least about 25 wt %, at least about 26 wt %, at least about 27 wt %, at least about 28 wt %, at least about 29 wt %, at least about 30 wt %, at least about 31 wt %, at least about 32 wt %, at least about 33 wt %, at least about 34 wt %, at least about 35 wt % of the non-animal derived components, such as for example Seagel® CAP 203, of the total weight of the shell.

Water is added to the gelatine and/or to the non-animal derived components to provide a liquid outer shell mixture that is easily manipulated and molded during the manufacturing process. In some embodiments, the outer shell comprises water. In certain embodiments, the outer shell has a water content of at least about 20 wt %, at least about 25 wt %, at least about 28 wt %, at least about 30 wt %, at least about 34 wt %, at least about 35 wt %, at least about 36 wt %, at least about 37 wt %, at least about 38 wt %, at least about 39 wt %, or at least about 39.5 wt % of the total weight of the outer shell.

The shell of the present disclosure, as initially prepared, generally comprises from about 10% to about 35% (w/w) plasticizer, preferably from about 15% to about 30% (w/w) plasticizer, and most preferably from about 20% to about 30% (w/w) plasticizer. A preferred plasticizer according to the present disclosure is glycerine. Another preferred plasticizer is sorbitol, sorbitan and/or a combination of sorbitol and sorbitan. In another preferred embodiment the plasticizer can be a mixture of glycerine, sorbitol and sorbitan.

In some embodiments, the outer shell comprises at least about 13.0 wt %, at least about 14.0 wt %, at least about 15.0 wt %, at least about 16.0 wt %, at least about 17.0 wt %, at least about 18.0 wt %, at least about 19.0 wt %, or at least about 20.0 wt % glycerin of the total weight of the outer shell.

Plasticizers including, but not limited to, glycerine and sorbitol-sorbitan solution can be added to the outer shell to confer the desired material properties of the final outer shell for handling, storage, and use. The soft shell thus obtained has the required flexibility characteristics for use as an encapsulation agent. Useful plasticizers of the present disclosure include glycerine, propylene glycol, sorbitan, sorbitol, or similar low molecular weight polyols, and mixtures thereof.

For example, glycerine and/or sorbitol-sorbitan may be added to increase the plasticity and pliability of the outer shell. In some embodiments, the outer shell comprises one or more plasticizers. In certain embodiments, the one or more plasticizers comprise glycerine. In other embodiments, the one or more plasticizers comprise sorbitol-sorbitan.

Currently there is a growing interest in using materials that avoid animal-derived products or compounds for formulation of the capsule shells to address cultural, religious, and dietary requirements. For example, Hydroxypropyl Methylcellulose as for example used in V—caps, Quali—VC and Vegicaps, as well as pullulan shells (NPCaps) and starch are alternatives that are envisaged as shell material without animal derived products. In a preferred embodiment of present disclosure, the shell therefore does not comprise any animal derived products. In one embodiment of present disclosure the shell comprises starch, carrageenan, Seagel® CAP 203, or combinations thereof.

In some embodiments the outer shell comprises at least about 13 wt %, at least about 14 wt %, at least about 15 wt %, at least about 16 wt %, at least about 17 wt %, at least about 18 wt %, at least about 19 wt %, at least about 20 wt %, at least about 21 wt %, at least about 22% wt %, at least about 23% wt %, at least about 24% wt % glycerine of the total weight of the outer shell, most preferred being an amount of at least about 25 wt % glycerine.

In some embodiments, the outer shell comprises colorants such as dyes or pigments. It should be recognized that any food-grade dye known in the art is suitable for use in the outer shell of the present disclosure.

In addition to dyes, other colorant agents may be included to increase the opacity of the outer shell to provide a more attractive appearance to the soft gel capsule. In other embodiments, the outer shell comprises titanium dioxide, starch, calcium carbonate, zinc oxide, tricalcium phosphate iron oxides, or combinations thereof. In one embodiment, the outer shell comprises a pearlescent pigment. In certain embodiments, the pearlescent pigment comprises a natural silicate or silica in combination with titanium oxide particles and/or iron oxide particles, wherein the particles have a particle size between about 5 microns and about 150 microns. In certain embodiments, the outer shell comprises a Candurin® pigment. In certain other embodiments, the outer shell comprises a silver or gold pearlescent pigment.

In a further embodiment the present disclosure also provides for soft gel capsules comprising an inner fill, an outer shell, and a coating, wherein the outer shell encapsulates the inner fill and the coating is applied to the outer shell. Coatings may be applied to the outer shell of the soft gel capsules as described herein for purposes including, but not limited to, further improvements to aesthetic appearance, flavour modification, ease of ingestion, capsule identification, etc. In some embodiments, the coating is a film-coating. In other embodiments, the coating is a pharmaceutical glaze. In other embodiments, the coating comprises food-grade shellac.

If it is desired to improve the taste of the soft gel capsule, flavourings and/or sweeteners may be added as a coating to the capsule. In other embodiments, the coating comprises one or more flavourings. In certain embodiments, the coating comprises sugar or an artificial sweetener.

The coating may further include ink for labelling and/or identification. In some embodiments, the coating comprises ink. In certain embodiments, the ink comprises polypropylene glycol.

The present disclosure also specifically relates to soft gel capsules comprising dietary supplements.

The dietary supplement can be any composition containing one or more vitamins, herbs, enzymes, amino acids, or other ingredients to be taken orally to supplement one's diet, as by providing a missing nutrient. The compositions according to the disclosure may contain at least two, three, four, five or at least six nutrients selected from the group consisting of or comprising: Iron (i.e. Carbonyl iron, Ferrous fumarate or Ferrous sulphate), Iodide (i.e. Potassium iodide or iodate), Magnesium (i.e. Magnesium oxide), Calcium (i.e Calcium carbonate), Zinc (i.e. Zinc oxide or Zinc sulphate), Selenite Copper (i.e. Sulphate copper or Copper oxide), DHA and EPA. Furthermore, the composition according to the disclosure may preferably contain at least two, three, four, five or at least six vitamins selected from the group consisting of or comprising: Vitamin A (i.e. Retinol palmitate or β-Carotene), Vitamin B1 (i.e. Thiamin or Thiamin mononitrate), Vitamin B2 (i.e. Riboflavin), Vitamin B3 (i.e. Nicotinamide), Vitamin B5 (as Pantothenic Acid or Calcium pantothenate), Vitamin B6 (i.e Pyridoxine or Pyridoxine hydrochloride), Vitamin B9 (i.e. Folic acid or Metafolin), Vitamin B12 (i.e. Cyanocobalamin), Vitamin H (i.e. Biotin), Vitamin D (i.e. Vitamin D3), Vitamin E (i.e. DL-α-Tocopheryl acetate, DL-α-Tocopherol or D-α-Tocopherol), Choline (i.e. Bitartrate choline), and Vitamin K.

In one embodiment of present disclosure the dietary supplement can be combined with the at least one active ingredient dissolved, suspended or solubilized in a solution comprising less than 50% (w/w) of water and less than 5% (w/w) of alcohol, preferably ethanol as further described herein above. In a preferred aspect of said embodiment the dietary supplement is combined with a plant extract comprising at least one of Matricaria flower liquid extract, Peppermint leaves liquid extract, Liquorice root liquid extract, Caraway fruit liquid extract, Bitter candytuft fresh plant liquid extract, Melissa leaf liquid extract, Chamomile flowers liquid extract, Liquorice root liquid extract, Lemon balm leaf liquid extract, Angelica root liquid extract, Celandine herb liquid extract, Milk thistle fruit liquid extract, or combinations thereof.

In one embodiment of present disclosure the opacifier is selected from starch, titanium dioxide, starch, calcium carbonate, Zinc oxide, tricalcium phosphate, iron oxides, or combinations thereof.

In one embodiment the colorants are selected from synthetic colorants or natural colorants. Exemplary synthetic colorants or lakes include but are not limited to FD&C Blue #1, D&C Red #33, D&C Red 40, FD&C yellow #6, D&C yellow #10. Exemplary natural colorants include, but are not limited to copper complexes of chlorophylls, carmine, caramel, carotenoids, Carthamus, carrot, xanthophylls, beetroot red, paprika extract, sorghum extract, vegetable carbon, annatto.

The water content of the soft gel capsules may be described by the water activity value that can be determined as further described in Example 3.

Water activity ($a_w$) is the partial vapor pressure of water in a solution divided by the standard state partial vapor pressure of water. Water activity, $a_w$, is a measure of how much of that water is free, i.e., unbound, and thus available to migrate to the shell. Standard moisture determination methods can be used to determine the total water content. However, water activity measurement was used by the inventors to give an insight into the impact of water on critical product quality attributes including stability, dissolution rate, and physical properties of the capsules. Water migrates from areas of high $a_w$ to areas of low $a_w$. As such the inventors have utilized the $a_w$ as a parameter for selecting the fill content of the present disclosure.

In order to minimize the water migration, the water activity of the fill shall ideally be close to the water activity of the shell.

In one embodiment of the pharmaceutical or dietary composition of present disclosure the water activity value of the fill is between 0.30 and 0.60, between 0.31 and 0.55, between 0.32 and 0.52, between 0.33 and 0.51, preferably between 0.35 and 0.50, more preferably between 0.37 and 0.47, most preferred between 0.38 and 0.45. In a preferred embodiment the water activity value of the fill is 0.39. In another preferred embodiment the water activity value of the fill is 0.45.

In a further embodiment of the pharmaceutical or dietary supplement composition of present disclosure the water activity value of the fill is between 0.70 and 0.90, preferably between 0.73 and 0.85, more preferably between 0.74 and 0.84, most preferred between 0.75 and 0.83. In a preferred embodiment the water activity value of the fill is 0.76. In another preferred embodiment the water activity value of the fill is 0.82 or 0.81.

In a preferred embodiment of the pharmaceutical or dietary supplement composition of present disclosure the fill comprises a) Iberogast N concentrate
b) at least one solubilizer, wherein the solubilizer is selected from Macrogol 600, sunflower oil, olive oil and maize oil, or combinations thereof; and
c) at least one thickening agent, wherein the thickening agent is selected from Macrogol 4000 and Geleol™ Mono and Diglycerides NF, colloidal silicone dioxide, beeswax or combinations thereof; and
d) wherein the shell comprises an edible polymer and/or plasticizer, and optionally an opacifier and/or colorants.

In another preferred embodiment of the pharmaceutical or dietary composition of present disclosure the fill comprises
a) Iberogast N concentrate
b) at least one solubilizer, wherein the solubilizer is selected from Macrogol 600, sunflower oil, olive oil and maize oil, or combinations thereof; and
c) at least one thickening agent, wherein the thickening agent is selected from Macrogol 4000 and Geleol™ Mono and Diglycerides NF, colloidal silicone dioxide, beeswax or combinations thereof; and
wherein the shell comprises an edible polymer selected from gelatine, gelatine RXL, gelatine GELITA® RXL R2 and non-animal derived compounds, such as Seagel® CAP 203, carrageenan, vegetable starch, such as for example maize or pea starch, or combinations thereof, preferably gelatine GELITA® RXL R2 or Seagel® CAP 203.

In one preferred embodiment of the pharmaceutical or dietary composition of present disclosure the fill comprises
a) Iberogast N concentrate; and
b) Macrogol 600; and
c) Colloidal silicon dioxide In a further preferred embodiment of the pharmaceutical or dietary composition of present disclosure the fill comprises
a) Iberogast N concentrate; and
b) Soya oil; and
c) Beeswax In a further preferred embodiment of the pharmaceutical or dietary composition of present disclosure the fill comprises
a) Iberogast N concentrate; and
b) Olive oil; and
c) Beeswax In a further preferred embodiment of the pharmaceutical or dietary composition of present disclosure the fill comprises
a) Iberogast N concentrate; and
b) Sunflower oil; and
c) Beeswax In a further preferred embodiment of the pharmaceutical or dietary composition of present disclosure the fill comprises
a) Iberogast N concentrate; and
b) Maize oil; and
c) Beeswax In a further preferred embodiment of the pharmaceutical or dietary composition of present disclosure the fill comprises
d) Iberogast N concentrate; and
e) Macrogol 600; and
f) Macrogol 4000

In a further preferred embodiment of the pharmaceutical or dietary composition of present disclosure the fill comprises
d) Iberogast N concentrate; and
e) Olive oil; and
f) Geleol™ Mono and Diglycerides NF In a further preferred embodiment of the pharmaceutical or dietary composition of present disclosure the fill comprises
a) Iberogast N concentrate; and b) Sunflower oil; and
c) Geleol™ Mono and Diglycerides NF In a further preferred embodiment of the pharmaceutical or dietary composition of present disclosure the fill comprises
a) Iberogast N concentrate; and
b) Maize oil; and
c) Geleol™ Mono and Diglycerides NF In a further preferred embodiment of the pharmaceutical or dietary composition of present disclosure the fill comprises
a) Iberogast N concentrate; and
b) soybean oil; and
c) Geleol™ Mono and Diglycerides NF In one preferred embodiment the shell comprises no animal derived products, most preferred being the use of Seagel® CAP 203.

In a preferred embodiment of the pharmaceutical or dietary composition of present disclosure the fill comprises
a) Iberogast N concentrate; and
b) olive oil; and
c) beeswax,
wherein the shell comprises Seagel® CAP 203.

In a further preferred embodiment of the pharmaceutical or dietary composition of present disclosure the fill comprises
a) Iberogast N concentrate; and
b) Macrogol 600; and
c) Colloidal silicone,
wherein the shell comprises gelatine GELITA® RXL R2, and optionally sorbitol sorbitan.

In a further preferred embodiment of the pharmaceutical or dietary composition of present disclosure the fill comprises
a) Iberogast N concentrate; and
b) Macrogol 600; and
c) Colloidal silicone,
wherein the shell comprises Gelatin RXL, and optionally sorbitol sorbitan.

In a preferred embodiment of the pharmaceutical or dietary composition of present disclosure the fill comprises
a) Iberogast N concentrate; and
b) soya oil; and
c) beeswax,
wherein the shell comprises gelatine GELITA® RXL R2, and optionally sorbitol sorbitan.

The present disclosure furthermore relates to a method of reducing brittleness of a softgel capsule as disclosed herein, wherein a solubilizer is added to the fill before encapsulation with the shell, wherein the solubilizer is selected from Macrogol 400, Macrogol 600, plant oils such as soybean oil, sunflower oil, olive oil and maize oil, preferably wherein the solubilizer is Macrogol 600, sunflower oil, olive oil or maize oil.

It has been shown by the inventors that by using a specific solubilizer in the fill compositions of present disclosure, namely hydrophilic fill compositions, the brittleness of the soft gel capsule caused by undesired fill and shell interaction can be reduced.

The above described migration between fill and shell also leads to fragile soft get capsules that do not comply with the industry standard. Adding a specific solubilizer to the fill compositions of present disclosure therefore also reduced the fragility of the soft gel capsules.

The present disclosure therefore also relates to a method of reducing the fragility of pharmaceutical or dietary supplement compositions in the form of a softgel gelatine capsule comprising a liquid or semisolid fill and a shell, the method comprising a step of adding a solubilizer to the fill before encapsulation with the shell, wherein the solubilizer is selected from polyethylene glycol 400, polyethylene glycol 600, plant oils such as soybean oil, sunflower oil, olive oil and maize oil, preferably wherein the solubilizer is polyethyelene glycol 600, sunflower oil, olive oil or maize oil.

The present disclosure furthermore relates to a pharmaceutical composition as described herein for use in the treatment of functional disorders of the gastrointestinal (GI) tract, such as functional dyspepsia (FD) and irritable bowel syndrome (IBS), minor gastro-intestinal complaints, such as bloating, minor spasms, a burning sensation, pain, inflammations, swelling and functional impairments accompanying diseases of the locomotor apparatus of rheumatic origin, such as rheumatoid arthritis, arthroses, spinal syndromes, epicondylitis, periarthritis, Bechterew's disease and/or lumbago.

In one preferred embodiment the disclosure relates to a pharmaceutical composition as disclosed herein, wherein the active ingredient is a plant extract comprising Matricaria flower liquid extract, Peppermint leaves liquid extract, Liquorice root liquid extract, Caraway fruit liquid extract, Bitter candytuft fresh plant liquid extract and Melissa leaf liquid extract, preferably wherein the active ingredient is Iberogast N concentrate, for use in the treatment of functional dyspepsia, minor gastro-intestinal complaints, such as bloating, minor spasms and/or a burning sensation.

In another preferred embodiment the disclosure relates to a pharmaceutical composition as disclosed herein, wherein the active ingredient is a plant extract comprising a mixture of Chamomile flowers liquid extract, Peppermint leaves liquid extract, Liquorice root liquid extract, Caraway fruit liquid extract, Bitter candytuft fresh plant liquid extract, Lemon balm leaf liquid extract, Angelica root liquid extract, Celandine herb liquid extract and Milk thistle fruit liquid extract for use in the treatment of functional disorders of the gastrointestinal (GI) tract, such as functional dyspepsia (FD) and irritable bowel syndrome (IBS).

In another preferred embodiment the disclosure relates to a pharmaceutical composition as disclosed herein, wherein the active ingredient is a plant extract comprising a mixture of American aspen or aspen stem bark and leaves liquid extract, Common ash stem bark liquid extract and European goldenrod herb liquid extract for use in the treatment of pain, inflammations, swelling and functional impairments accompanying diseases of the locomotor apparatus of rheumatic origin, such as rheumatoid arthritis, arthroses, spinal syndromes, epicondylitis, periarthritis, Bechterew's disease and/or lumbago.

The soft shells of the present disclosure comprising gelatine can be prepared by combining appropriate amounts of gelatine, water, plasticizer, and any optional components in a suitable vessel and agitating and/or stirring while heating to about 65° C., until a uniform solution is obtained. This soft gelatine shell preparation can then be used for encapsulating the desired quantity of the fill composition employing standard encapsulation methodology to produce one-piece, hermetically sealed, soft gelatine capsules. The gelatine capsules are formed into the desired shape and size so that they can be readily swallowed. The soft gelatine capsules of the instant disclosure are of a suitable size for easy swallowing and typically contain from about 100 mg to about 2000 mg of the active composition. Soft gelatine capsules and encapsulation methods are described in P. K. Wilkinson et at., "Softgels: Manufacturing Considerations", Drugs and the Pharmaceutical Sciences, 41 (Specialized Drug Delivery Systems), P. Tyle, Ed. (Marcel Dekker, Inc., New York, 1990) pp. 409-449; F. S. Horn et at., "Capsules, Soft", Encyclopedia of Pharmaceutical Technology, vol. 2, J. Swarbrick and J. C. Boylan, eds. (Marcel Dekker, Inc., New York, 1990) pp. 269-284; M. S. Patel et at., "Advances in Softgel Formulation Technology", Manufacturing Chemist, vol. 60, no. 7, pp. 26-28 (July 1989); M. S. Patel et al., "Softgel Technology", Manufacturing Chemist, vol. 60, no. 8, pp. 47-49 (August 1989); R. F. Jimerson, "Softgel (Soft Gelatin Capsule) Update", Drug Development and Industrial Pharmacy (Interphex '86 Conference), vol. 12, no. 8 & 9, pp. 1133-1144 (1986); and W. R. Ebert, "Soft Elastic Gelatin Capsules: A Unique Dosage Form", Pharmaceutical Technology, vol. 1, no. 5, pp. 44-50 (1977); these references are incorporated by reference herein in their entirety. The resulting soft gelatin capsule is soluble in water and in gastrointestinal fluids. Upon swallowing the capsule, the gelatin shell rapidly dissolves or ruptures in the gastrointestinal tract thereby introducing the pharmaceutical actives from the liquid core into the physiological system.

The vegetarian or vegan soft shells of the present disclosure that do not comprise gelatine from animal sources, can be prepared as described above, the melting temperature being around 95° C.

Preferably the capsules have an oblong or oval shape to facilitate swallowing. In the case of a capsule containing 300 to 700 mg of the combined active ingredients an oblong capsule may be about 10.0-20.0 mm, preferably 12.0-18.0 mm, in particular about 15.0 to 15.5 mm long and have a diameter of about 5.0 to 11.0 mm, preferably 6.0-10.0 mm, in particular 8.0-9.0 mm, most preferred 8.8 to 9.0 mm.

In one embodiment of present disclosure, the soft gel capsule may be characterized by standard shape and size categories known in the art to describe soft gel capsule forms and fill values. In some embodiments, the soft gel capsule may have a shape that is oval, oblong, or round. In certain embodiments, the soft gel capsule may have a size between 12 and 18 minims. In some embodiments, the soft gel capsule has a size of less than or equal to an oval, oblong, or round size 12 minims gel capsule. In certain embodiments, the soft gel capsule has a size and shape of 12 minims oval or 12 minims oblong. In some embodiments, the soft gel capsule has a size and shape of 12 minims oblong. In other embodiments, the soft gel capsule has a size of less than or equal to an oval, oblong, or round size 18 minims capsule. In certain embodiments, the soft gel capsule has a size and shape of 18 minims oval or 18 minims oblong. In still other embodiments, the soft gel capsule has a size and shape of 18 minims oblong.

It is finally contemplated that any features described herein can optionally be combined with any of the embodiments of any method, medical use, kit and use of a kit of the disclosure; and any embodiment discussed in this specification can be implemented with respect to any of these. It will be understood that particular embodiments described herein are shown by way of illustration and not as limitations of the disclosure.

All publications and patent applications are herein incorporated by reference to the same extent as if each individual publication or patent application was specifically and individually indicated to be incorporated by reference.

The use of the word "a" or "an" may mean "one," but it is also consistent with the meaning of "one or more," "at least one," and "one or more than one". The use of the term "another" may also refer to one or more. The use of the term "or" in the claims is used to mean "and/or" unless explicitly indicated to refer to alternatives only or the alternatives are mutually exclusive.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. The term "comprises" also encompasses and expressly discloses the terms "consists of" and "consists essentially of". As used herein, the phrase "consisting essentially of" limits the scope of a claim to the specified materials or steps and those that do not materially affect the basic and novel characteristic(s) of the claimed disclosure. As used herein, the phrase "consisting of" excludes any element, step, or ingredient not specified in the claim except for, e.g., impurities ordinarily associated with the element or limitation.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

As used herein, words of approximation such as, without limitation, "about", "around", "approximately" refers to a condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skilled in the art recognize the modified feature as still having the required characteristics and capabilities of the unmodified feature. In general, but subject to the preceding discussion, a numerical value herein that is modified by a word of approximation such as "about" may vary from the stated value by ±1, 2, 3, 4, 5, 6, 7, 8, 9, or 10%. Accordingly, the term "about" may mean the indicated value ±5% of its value, preferably the indicated value ±2% of its value, most preferably the term "about" means exactly the indicated value (±0%).

EXAMPLES

Example 1: Development of a Formulation to Encapsulate Iberogast® in a Soft Gelatin Capsule The aim was to develop a feasible formulation to encapsulate Iberogast® in a soft gelatine capsule. Iberogast® is a multi-drug-combination with herbal extracts, is used to treat functional dyspepsia in the forms of indigestion, stomach pain, bloating and gas. The target product has to have the following main characteristics:

Fill and shell formulations have to minimize the loss of water and alcohol.
Trying to keep a maximum of 2 capsules per dose.

The main challenge that Iberogast® exhibits for developing in soft gelatine capsule is the high ethanol and water content, 31% (v/v) ethanol—240 mg per dosage and around 66% of water. However, the amount of ethanol that can be filled into soft gelatine capsules is limited to less than 15% because ethanol can diffuse out of a capsule due to its volatility.

Previous compatibility and solubility tests were performed and showed that:

The Iberogast® formula "as is" dissolves the shell in 48 h. Above 30° C. no shell was found Iberogast® is not soluble in soya oil and in Medium-chain triglycerides (50:50 w/w)

Iberogast® is soluble in Macrogol (50:50). However, after 24 h a cloudy phase was observed The compatibility test of the solution Iberogast®/Macrogol (50:50 w/w) was successful, the shell keeps the integrity at room temperature and 30° C. for 48 h.

Based on analytical results, physical-chemical parameters, compatibility test and considering the colour customer requirements two formulations were selected as prototypes as shown in the tables below:

TABLE 1

Shell and fill composition of the pilot batch V-G1; size 14 oblong

| | V-G1 |
|---|---|
| Fill | mg/cp |
| Iberogast ® | 492.50 |
| Macrogol 400 | 492.50 |
| Total | 985.00 |
| Shell | % |
| Gelatin | 45.00 |
| Sorbitol sorbitan solution | 12.00 |
| Glycerin | 12.00 |
| Titanium dioxide | 0.40 |
| Chlorophyllins E-141 (ii) | 0.30 |
| Iron oxide | 0.10 |
| Purified water | 30.20 |
| Total | 100.00 |

TABLE 2

Shell and fill composition of the pilot batch V-G2; size 14 oblong

| | V-G2 |
|---|---|
| Fill | mg/cp |
| Iberogast ® | 492.50 |
| Macrogol 400 | 392.50 |
| Poly-n-vinylpyrrolidone K30 | 100.00 |
| Total | 985.00 |
| Shell | % |
| Gelatin | 45.00 |
| Sorbitol sorbitan solution | 12.00 |
| Glycerin | 12.00 |
| Titanium dioxide | 0.40 |
| Chlorophyllins E-141 (ii) | 0.30 |
| Iron oxide | 0.10 |
| Purified water | 30.20 |
| Total | 100.00 |

Due to the loss of ethanol and water during the drying process, the capsules from batches G1 and G2 showed misshapenness after manufacturing.

To assess whether the reduction in size would improve the capsules appearance two additional batches with reduced capsules size were manufactured. Batch V-G3 was encapsulated in 12 oval mold and batch V-G4 in 12 oblong. Table 3 shows fill and shell formulations of batches V-G3 and V-G4.

TABLE 3

Shell and fill composition of the pilot batch V-G3 and V-G4

| | V-G3 & V-G4 |
|---|---|
| Fill | mg/cp |
| Iberogast ® | 492.50 |
| Macrogol 400 | 492.50 |
| Total | 985.00 |
| Shell | % |
| Gelatin | 45.00 |
| Sorbitol sorbitan solution | 12.00 |
| Glycerin | 12.00 |
| Titanium dioxide | 0.40 |
| Chlorophyllins E-141 (ii) | 0.30 |
| Iron oxide | 0.10 |
| Purified water | 30.20 |
| Total | 100.00 |

During the manufacture of the batches V-G3 and V-G4 no improvements were reached by chaining the mold or modifying the dynamic drying time between 1 and 2 hours. After drying process capsules exhibit a significant loss of weight resulting in capsules deformed and shrinks due to the water loss.

A further attempt consisting of modifying shell formulation and drying process were made. Two additional batches were manufactured V-G6 and V-G7. Table 4 and 5 show their fill and shell formulations.

TABLE 4

Shell and fill composition of the pilot batch V-G6

| | V-G6 |
|---|---|
| Fill | mg/cp |
| Iberogast ® | 492.50 |
| Macrogol 400 | 492.00 |
| Total | 984.50 |
| Shell | % |
| Gelatin | 42.00 |
| Gelatin Sol P | 3.00 |
| Sorbitol sorbitan solution | 12.00 |
| Glycerin | 12.00 |
| Purified water | 31.00 |
| Total | 100.00 |

TABLE 5

Shell and fill composition of the pilot batch V-G7

| | V-G7 |
|---|---|
| Fill | mg/cp |
| Iberogast ® | 492.50 |
| Macrogol 400 | 492.00 |
| Total | 984.50 |
| Shell | % |
| Gelatin | 29.80 |
| Glycerin | 32.30 |
| Corn starch | 12.00 |
| Purified water | 25.90 |
| Total | 100.00 |

Corn starch was included in pilot batch V-G7 to improve the elasticity of the shell and minimize the misshaped of the capsules during drying.

The following drying trials modifying the drying conditions were performed:
Standard (dynamic+static drying 20° C./20% RH)
Dynamic drying
Dynamic drying+25° C./60% RH slow drying in climatic chamber
Dynamic drying+30° C./65% RH slow drying in climatic chamber However, none of these attempts were successful, as all capsules were still misshaped after performing the drying steps.

Example 2: Iberogast N Concentrate in Soft Gelatin Capsule

TABLE 6

Iberogast N composition

| Drug substance | ml | % |
|---|---|---|
| Ethanolic extract of fresh plants of bitter candytuft (1:1.5-2.5) extracting agent: Ethanol 50% (v/v) | 15 | 15 |
| Ethanolic extract of melissa leaf (1:2.5-3.5) extracting agent: Ethanol 30% (v/v) | 15 | 15 |
| Ethanolic extract of caraway fruit (1:2.5-3.5) extracting agent: Ethanol 30% (v/v) | 20 | 20 |
| Ethanolic extract of liquorice root (1:2.5-3.5) extracting agent: Ethanol 30% (v/v) | 10 | 10 |
| Ethanolic extract of matricaria flower (1:2-4) extracting agent: Ethanol 30% (v/v) | 30 | 30 |
| Ethanolic extract of peppermint leaf (1:2.5-3.5) extracting agent: Ethanol 30% (v/v) | 10 | 10 |
| Total | 100 | 100 |

Iberogast N concentrate is the product of the distillation process of Iberogast N to eliminate ethanol and reduce water content to obtain a feasible material to be encapsulated in a soft gelatin capsule. During the manufacturing process, the active ingredient Iberogast N is concentrated by distillation being the Iberogast N dosage of 1 ml transformed around 78 to 82 μl of Iberogast N concentrate. The conversions in mg take into consideration the density of the Iberogast N concentrate set in the raw material specification (1.20-1.30 g/ml). A description of the distillation process used can be found in Gaedcke & Steinhoff: "Herbal Medicinal Products" (2003), medpharm GmbH Scientific publishers.

TABLE 7

Extract specifications of Iberogast ® and Iberogast N concentrate:

|  | Iberogast ® | Iberogast N concentrate |
|---|---|---|
| Water content (%) w/w | ~68 | 45-50 |
| Ethanol content | 29.5-32.6% | <2 g/100 g |
| Dry residue (%) w/w | ~5.4 | 50-55 |
| Density (g/ml) | 0.975-0.995 | 1.20-1.30 |

Despite the reduction in ethanol and water content, the amount of water makes the Iberogast N concentrate not feasible to be directly encapsulated in soft gel. The amount of water is far above the recommended value. To avoid the misshapenness of the capsules, development trials were conducted to minimize the interaction of the Iberogast N concentrate with the shell and obtain a feasible fill formulation. Attending to the miscibility of Iberogast N concentrate in hydrophilic excipients, the formulation selected for prototyping is shown in table 8.

TABLE 8

Shell and fill composition of the batch E-G2

| Fill | E-G2 mg/cp |
|---|---|
| Iberogast N concentrate | 101.72 |
| Macrogol 400 | 434.03 |
| Colloidal Silicone dioxide | 13.75 |
| Total | 549.50 |

| Shell | % |
|---|---|
| Gelatin | 43.50 |
| Glycerin | 20.00 |
| Corn starch | 2.00 |
| Purified water | 34.50 |
| Total | 100.00 |

A physical stability study was conducted with prototype E-G2 for 12 months; fragility of the capsules was observed from capsules release.

Fragility Test

The fragility test is an internal test developed to evaluate capsule brittleness. The method consists of placing the capsules on a metal platform in such a way that the seam is always parallel to the plate. The placement of the capsule is critical to the test due to its influence in the results. The capsule is positioned in the centre of a methacrylate tube with an internal diameter of 30 mm and a height of 100 mm. A calibrated weight of 100 g is placed over a platform on the top of the tube. Then, the platform is opened to leave the free fall of the weight on the capsule. After the fall, the integrity of the capsule is checked. A representative sample of 25 capsules is submitted to the test and the result is expressed as the percentage of broken capsules.

Flexibility Test

Flexibility of the capsules measures the resistance of the capsules when a compressive force is applied to produce a deformation of 2 mm, the resistance value is expressed in Newtons (N) and represents the hardness of the capsule. The flexibility is measured in 10 capsules using a hardness testing Bareiss Digi Test Gelomat.

Disintegration Test

Disintegration test is performed following the procedure described in the Ph Eur monograph 2.9.1. The disintegration test determines whether capsules disintegrate within the prescribed time when placed in a liquid medium in the experimental conditions prescribed below.

Use apparatus A.

Temperature of the liquid at 35-39° C.

Liquid test water. If the test fails using water as disintegration media, synthetic gastric juice media can be used.

Disintegration is considered to be achieved when: only fragments of shell remain on the screen; if a disc has been used fragments of shell may adhere to the lower surface of the disc.

Specification: To pass the test, all 6 of the capsules must have disintegrated in 30 min

TABLE 9

Summary of physicochemical parameters tested in prototype E-G2 for capsules packaged in blister aluminium/PVDC.

| Parameter | Time 0 | 12 months 25° C.-60% HR | 12 months 30° C.-65% HR | 12 months 30° C.-75% HR | 6 months 40° C.-75% HR |
|---|---|---|---|---|---|
| Flexibility (N) | 5.1 | 8.9 | 2.5 | 1.9 | 1.6 |
| Fragility test (% of broken capsules) | 0% (n = 25) w = 100 g | 100% (n = 25) w = 100 g | 0% (n = 25) w = 100 g | 0% (n = 25) w = 100 g | 0% (n = 25) w = 100 g |
| Disintegration test (h:min:sg) (Disintegration media) | 0:05:09 (water) | 0:08:16 (water) | 0:16:38 (gastric juice) | 0:25:30 (gastric juice) | Fail (gastric juice) |

Fragility of the capsules is detected during the stability study. Brittleness is due to fill and shell interactions. From encapsulation, water and plasticizer are prone to migrate inside the fill, hygroscopicity of the fill is a driving force for that process. In addition, Iberogast N concentrate migrates to the shell. Afterwards, during storage, atmospheric conditions play a key role in the dynamic of water migrations. In light of the results, it can be considered that the issue of brittleness of the capsule is related to migration phenomena between fill and shell.

Example 3: Oily and Hygroscopic Fills

The aim was to develop fill and shell formulations to improve capsules behaviour regarding the brittleness observed in batch E-G2. The development study established trials to decrease capsules brittleness.

Materials Tested
Vehicle/Solubilizer

Macrogol 600 (Polyethylene Glycol 600 (a-Hydro-o-hydroxypoly (oxy-1,2-ethanediyl))). Clear, viscous, colourless or almost colourless hygroscopic liquid. Miscible with water, very soluble in acetone, in alcohol, and in methylene chloride, practically insoluble in fatty oils and in mineral oils.

Poloxamer 124 is a non-ionic surfactant which contains hydrophilic and lipophilic groups. Therefore, it is miscible with water, alcohols and many oils. Poloxamer 124 is physiologically safe and stable against alkaline salts and acids. Colourless or almost colourless liquid.

Soybean Oil is a clear, pale-yellow colored, odorless or almost odorless liquid, with bland taste that solidifies between −10 and −16° C. with a viscosity value of 50.09 (25° C.) (mPa.$). Emulsions or suspensions containing soybean oil have been used as vehicles for the oral administration of drugs. Soybean oil is a stable material regarded as an essentially nontoxic and nonirritant material.

Emulsifying & Viscosity—Increasing Agents

Colloidal silicon dioxide: A light, fine, white or almost white, amorphous powder, with a particle size of about 15 nm, practically insoluble in water and in mineral acids except hydrofluoric acid. It dissolves in hot solutions of alkali hydroxides. Colloidal silicon dioxide is also used to stabilize emulsions and as a thixotropic thickening and suspending agent in gels and semisolid preparations.

Macrogolglycerol hydroxystearate is a non-ionic solubilizer and emulsifier. It is soluble in water and alcohol and miscible with a lot of lipoid-soluble substances. White or yellowish semi-liquid or pasty mass.

Povidone: Povidone (1-Ethenyl-2-pyrrolidinone homopolymer) is a synthetic polymer, which is used to enhance the solubility of active ingredients in hydrophilic vehicles. Different degree of polymerization results in polymers of various molecular weights, ranging from 2,500 to 3,000,000. It is characterized by its viscosity in aqueous solution, relative to that of water, expressed as a K-value, in the range 10-120. The ability of povidone to form a water-soluble complex with active substances can be used in pharmaceuticals to improve the release rate, the solubility of drugs and as an inhibitor of crystallization of the drug substances. The viscosity of a fill formulation can be controlled through the selection of appropriate molecular weight and concentration of the polymer.

Beeswax consists of 70-75% of a mixture of various esters of straight-chain monohydric alcohols with even-numbered carbon chains from 024 to 036 esterified with straight-chain acid. Beeswax is used as a thickening agent to prevent settling out of particulate matter. Beeswax is regarded as an essentially nontoxic and nonirritant material. It is included in the FDA Inactive Ingredients Database.

Fill Formulations Tested

Fill formulations were tested by combining solvents and emulsifying and/or viscosity increasing agent manufacturing fill formulations of around 200 g. The suitability of the fill formulation was evaluated by testing the physicochemical parameters as described below.

TABLE 10

Fill formulations tested

| Fill | Trial 1 (E-G2) Reference formulation mg/cp | Trial 2 mg/cp | Trial 3 mg/cp | Trial 4 mg/cp | Trial 5 mg/cp |
|---|---|---|---|---|---|
| Iberogast N concentrate | 100.00 | 100.00 | 100.00 | 100.00 | 100.00 |
| Macrogol 400 | 435.75 | — | — | — | — |
| Macrogol 600 | — | 440.50 | 374.50 | — | — |
| Colloidal Silicone dioxide | 13.75 | 9.00 | — | — | — |
| Povidone K12 | — | — | 75.00 | — | — |
| Poloxamer 124 | — | — | — | 419.50 | — |
| Macrogolglycerol hydroxystearate | — | — | — | 30.00 | — |
| Soyabean oil | — | — | — | — | 409.50 |
| Beeswax | — | — | — | — | 40.00 |
| Total | 549.50 | 549.50 | 549.50 | 549.50 | 549.50 |

Physicochemical Parameters

The following parameters of the above formulations were assessed:

a) Appearance

The Macroscopic appearance of the fill was photographically documented. The target appearance was a brown homogeneous suspension or solution.

b) Flow Tests

The viscosity was measured using a Ford cup #4 at 30° C.±2° C. to measure the viscosity by measuring the timed flow of a known volume of liquid passing through an orifice located at the bottom. Specification: The fill flows without interruption.

c) Dynamic Viscosity

The dynamic viscosity was measured with a digital rotary viscometer Brookfield DV II; 30° C.±2° C. The recommended range was NMT 4000 cPs.

d) Density at 30° C.

This test was performed as informative parameter to estimate the final volume of the capsule. It was performed in a 10 mL volumetric flask at 30° C.±2° C.

e) pH

The pH of the fill formulation was measured directly in hygroscopic fills whereas in oily fill it was measured in water dispersion at 10% w/w.

f) Water Activity

A representative sample of each fill was taken to obtain the amount of sample needed for the water activity assay. The test sample was homogenized and tested quickly after sample taking to avoid water intake from the environment. The water activity was determined using AquaLab TDL equipment according to the instructions provided.

g) Phase Separation

Around 2-3 gr of each fill formulation was kept in a test tube at 30° C. and 40° C. for 24 h or 72 h and it was observed if any phase separation was produced.

Fill candidates for pilot batches will be confirmed if the formulation has good flow properties without phase separation and viscosity values NMT 4000 cPs.

Results

Table 11 shows the physicochemical parameters of the fill formulations tested. Based on the criteria established to select fill formulation for prototyping. The fill formulations corresponding with trial 2 and trial 5 were considered feasible for moving forward to the manufacture of pilot batches.

TABLE 11

| Fill | Trial 1 (E-G2) Reference formulation Result | Trial 2 Result | Trial 3 Result | Trial 4 Result | Trial 5 Result |
| --- | --- | --- | --- | --- | --- |
| Appearance | Homogeneous suspension | Homogeneous suspension | Homogeneous suspension | Homogeneous suspension | Homogeneous suspension |
| Fluidity at 30° C. (s) | 281 | 184 | 154 | 202 | 182 |
| Viscosity at 30° C. (cPs) | 2409 | 1309 | 758 | 826 | 1944 |
| Density at 30° C. (g/ml) | 1.17 | 1.16 | 1.16 | 1.08 | 0.96 |
| pH | 6.82 | 6.89 | 7.01 | 6.15 | 5.60 |
| Water (%) | 7.10 | 6.90 | 7.60 | 6.05 | 2.61 |
| $a_w$ | 0.3637 | 0.3903 | 0.3957 | 0.5975 | 0.7633 |
| Phase separation at 30° C. & 40° C. | No phase separation | No phase separation | Slightly phase separation | Fail test (Paste residues) | No phase separation |

The resulting fill and shell formulations selected for prototyping are reported in tables 12-14. Colorants are included in shell composition of the batch G5 to avoid seeing the internal phase separation.

TABLE 12

Shell and fill composition of pilot batch E-G3

| Fill | E-G3 mg/cp |
| --- | --- |
| Iberogast N concentrate | 100.0 |
| Soya oil | 409.5 |
| Beeswax | 40.00 |
| Total | 549.50 |

| Shell | % |
| --- | --- |
| Gelatin | 43.50 |
| Glycerin | 20.00 |
| Purified water | 36.50 |
| Total | 100.00 |

TABLE 13

Shell and fill composition of pilot batch E-G5

| Fill | E-G5 mg/cp |
| --- | --- |
| Iberogast N concentrate | 100.0 |
| Soya oil | 409.50 |
| Beeswax | 40.00 |
| Total | 549.50 |

| Shell | % |
| --- | --- |
| Gelatin | 43.50 |
| Glycerin | 20.00 |
| Iron oxide red | 0.35 |
| Iron oxide black | 0.12 |
| Purified water | 36.03 |
| Total | 100.00 |

TABLE 14

Shell and fill composition of pilot batch E-G6

| Fill | E-G6 mg/cp |
| --- | --- |
| Iberogast N concentrate | 100.0 |
| Macrogol 600 | 440.50 |
| Colloidal Silicone dioxide | 9.00 |
| Total | 549.50 |

| Shell | % |
| --- | --- |
| Gelatin | 43.50 |
| Glycerin | 20.00 |
| Purified water | 36.50 |
| Total | 100.00 |

As can be seen in the below tables, the capsules do not show brittleness at none of the assessed storage conditions, physical stability studies are currently still ongoing.

TABLE 15

Physicochemical parameters of pilot batch E-G3:

| Parameter | Time 0 | 12 months 25° C.-60% HR | 12 months 30° C.-75% HR | 6 months 40° C.-75% HR |
| --- | --- | --- | --- | --- |
| Flexibility (N) | 6.4 | 2.3 | 1.5 | 1.2 |
| Fragility test (% of broken capsules) | 0% (n = 25) w = 100 g | 0% (n = 25) w = 100 g | 0% (n = 25) w = 100 g | 0% (n = 25) w = 100 g |
| Disintegration test (h:min:sg) (Disintegration media) | 0:06:22 (water) | 0:05:13 (water) | 0:05:57 (water) | 0:05:00 (water) |

TABLE 16

Physicochemical parameters of pilot batch E-G5:

| Parameter | Time 0 | 9 months 25° C.-60% HR | 9 months 30° C.-75% HR | 6 months 40° C.-75% HR |
| --- | --- | --- | --- | --- |
| Flexibility (N) | 3.0 | 2.6 | 1.5 | 1.3 |
| Fragility test (% of broken capsules) | 0% (n = 25) w = 100 g | 0% (n = 25) w = 100 g | 0% (n = 25) w = 100 g | 0% (n = 25) w = 100 g |
| Disintegration | 0:07:37 | 0:05:58 | 0:05:51 | 0:10:41 |

TABLE 16-continued

Physicochemical parameters of pilot batch E-G5:

| Parameter | Time 0 | 9 months 25° C.- 60% HR | 9 months 30° C.- 75% HR | 6 months 40° C.- 75% HR |
|---|---|---|---|---|
| test (h:min:sg) (Disintegration media) | (water) | (water) | (water) | (water) |

TABLE 17

Physicochemical parameters of pilot batch E-G6:

| Parameter | Time 0 | 9 months 25° C.- 60% HR | 9 months 30° C.- 75% HR | 6 months 40° C.- 75% HR |
|---|---|---|---|---|
| Flexibility (N) | 7.7 | 13.1 | 11.4 | 3.1 |
| Fragility test (% of broken capsules) | 0% (n = 25) w = 100 g | 0% (n = 25) w = 100 g | 0% (n = 25) w = 100 g | 0% (n = 25) w = 100 g |
| Disintegration test (h:min:sg) (Disintegration media) | 0:06:21 (water) | 0:05:48 (water) | 0:20:47 (water) | Fail (gastric juice) |

The tests performed with batches E-G3 and E-G5 containing an oily fill formulation can be summarized as follows:
  Disintegration test met specification
  Capsules do not show brittleness
  Capsule flexibility decreases during storage having lower values than (~2 N) the expected (~7 N)
  Capsules show stickiness
  Capsule appearance of the batch G3 shows phase separation The tests performed with batch E-G6 containing a hygroscopic fill formulation can be summarized as follows:
  Disintegration test does not met specification
  Capsules do not show brittleness
  Capsule flexibility increased during storage Based on these results further formulations were produced, see Example 4.

Example 4: Further Formulations with Oily and Hygroscopic Fills

The aim was to develop further formulations to improve capsules behaviour regarding the brittleness observed in batch E-G2 and stickiness and phase separation in batch E-G3 and E-G5. The development study established new trials to:
  Decrease capsules brittleness of the hydroscopic fill by increasing the molecular weight of polyethylene glycol and replacing colloidal silicon dioxide (considering as nanomaterial) by semisolid polyethylene glycol, (polyethylene glycol 4000).
  Decrease stickiness by increasing capsules flexibility and avoid or minimize phase separation of the oily fill. Replacing soya oil, which can be considered as an allergen, by alternative oils (sunflower, olive and maize oils). Replacing beeswax (animal origin) by other thickening agent from no animal source (Geleol Mono and Diglycerides NF, Gelucire 50/13, Gelucire 44/14 and hard fat).

Materials Tested
Vehicle/Solubilizer
  Macrogol 600 (as Per Example 3)
  Sunflower Oil—Fatty oil obtained from the seeds of *Helianthus annuus* by mechanical expression or by extraction. It is then refined. A suitable antioxidant may be added. Clear, light yellow liquid practically insoluble in water and in ethanol (96 percent) miscible with light petroleum (bp: 40-60° C.).
  Olive oil—Fatty oil obtained by refining of crude olive oil, obtained by cold expression or other suitable mechanical means from the ripe drupes of *Olea europaea*. A suitable antioxidant may be added. Clear, colourless or greenish-yellow transparent liquid practically insoluble in ethanol (96 percent), miscible with light petroleum (bp: 50-70° C.). When cooled, it begins to become cloudy at 10° C. and becomes a butter-like mass at about 0° C.
  Maize oil—Fatty oil obtained from the seeds of *Zea mays* by expression or by extraction. It is then refined. Clear, light yellow or yellow oil, practically insoluble in water and in ethanol (96 percent), miscible with light petroleum (bp: 40-60° C.) and with methylene chloride.
Emulsifying & Viscosity-Increasing Agents
  Geleol™ mono and diglycerides NF—(Glycerol monostearate 40-55 (Type I) EP/Mono and diglycerides NF) is a modified release matrix former for capsules. It can be used as a coating agent for taste masking or as a consistency agent. Safety of use is inferred by GRAS status and precedence of use in approved pharmaceutical products.
  Hard fat—Mixture of triglycerides, diglycerides and monoglycerides, which may be obtained either by esterification of hydrogenated fatty acids of vegetable origin with glycerol or by interesterification of hydrogenated vegetable oils. Each type of hard fat is characterized by its melting point, its hydroxyl value and its saponification value. It does not contain additives. White or almost white, waxy, brittle mass, practically insoluble in water, slightly soluble in anhydrous ethanol and in methylene chloride. When heated to 50° C. it melts, giving a colourless or slightly yellowish liquid.
  Gelucire® 44/14—(lauroyl polyoxyl-32 glycerides) is considered as an emulsifying agent; modified-release agent; nonionic water-dispersible surfactant for lipid-based formulations to solubilize and increase oral bioavailability of poorly water-soluble APIs. Self-emulsifies in aqueous media forming a fine dispersion, i.e., microemulsion (SMEDDS).
  Lauroyl polyoxylglycerides—USFA excipients, US Food additives according to 172.736 Food Additives Permitted For Direct Addition to Food for Human Consumption: Glycerides and Polyglycides of hydrogenated vegetable oils. Consists of a small fraction of mono, di- and triglycerides and mainly PEG-32 (MW 1500) mono- and diesters of lauric acid (C12). It is considered a Solubilizer for poorly-soluble APIs and bioavailability enhancer. Single excipient formulation system: self-emulsifies in aqueous fluid into microemulsion—LFCS Type III (SMEDDS).
  Gelucire® 50/13—(Stearoyl macrogol-32 glycerides) Solubilizer for poorly-soluble APIs and bioavailability enhancer. Single excipient formulation system self-emulsifies in aqueous fluid into coarse emulsion—LFCS Type III (SMEDDS). Modulation of drug release. Lipid binder in melt processes. Safety of use is inferred by toxicological data and precedence of use in approved pharmaceutical products.
  Stearoyl macrogol-32 glycerides—is a USFA excipient US Food additives according to 172.736 Food Additives Permitted For Direct Addition to Food for Human Consumption: Glycerides and Polyglycides.

Macrogol 4000—(Polyethylene Glycol 4000 (a-Hydro-o-hydroxypoly (oxy-1,2-ethanediyl))) white or almost white solid with a waxy or paraffin-like appearance. Miscible with water, very soluble in acetone, in alcohol, and in methylene chloride, practically insoluble in fatty oils and in mineral oils.

Fill Formulations Tested

Fill formulations were tested by combining solvents and emulsifying and/or viscosity increasing agent manufacturing fill formulations of around 200 g. The suitability of the fill formulation was evaluated by testing the physicochemical parameters as described below. Tables 17-22 summarize the fill formulations tested.

TABLE 18

Hygroscopic fills with macrogol excipients

| Fill | I&D-0090-21 mg/cp | I&D-0091-21 mg/cp | I&D-0107-21 mg/cp |
|---|---|---|---|
| Iberogast N concentrate | 100.00 | 100.00 | 100.00 |
| Macrogol 600 | 400.00 | 410.00 | 415.00 |
| Macrogol 4000 | 50.00 | 40.00 | 35.00 |
| Total | 550.00 | 550.00 | 550.00 |

TABLE 19

Fill formulation trials with Geleol ™ mono and diglycerides NF

| Fill | I&D-0092-21 mg/cp | I&D-0093-21 mg/cp | I&D-0094-21 mg/cp |
|---|---|---|---|
| Iberogast N concentrate | 100.00 | 100.00 | 100.00 |
| Olive oil | 410.00 | — | — |
| Sunflower oil | — | 410.00 | — |
| Maize oil | — | — | 410.00 |
| Geleol mono and diglycerides | 40.00 | 40.00 | 40.00 |
| Total | 550.00 | 550.00 | 550.00 |

TABLE 20

Fill formulation trials with Geleol mono and diglycerides NF

| Fill | I&D-0108-21 mg/cp | I&D-0109-21 mg/cp | I&D-0110-21 mg/cp |
|---|---|---|---|
| Iberogast N concentrate | 100.00 | 100.00 | 100.00 |
| Olive oil | 420.00 | — | — |
| Sunflower oil | — | 420.00 | — |
| Maize oil | — | — | 420.00 |
| Geleol mono and diglycerides | 30.00 | 30.00 | 30.00 |
| Total | 550.00 | 550.00 | 550.00 |

TABLE 21

Fill formulation trials with Hard fat

| Fill | I&D-0095-21 mg/cp | I&D-0096-21 mg/cp | I&D-0097-21 mg/cp |
|---|---|---|---|
| Iberogast N concentrate | 100.00 | 100.00 | 100.00 |
| Olive oil | 250.00 | — | — |
| Sunflower oil | — | 250.00 | — |
| Maize oil | — | — | 250.00 |
| Hard Fat | 200.00 | 200.00 | 200.00 |
| Total | 550.00 | 550.00 | 550.00 |

TABLE 22

Fill formulation trials with Gelucire 50/13

| Fill | I&D-0098-21 mg/cp | I&D-0099-21 mg/cp | I&D-0100-21 mg/cp |
|---|---|---|---|
| Iberogast N concentrate | 100.00 | 100.00 | 100.00 |
| Olive oil | 395.00 | — | — |
| Sunflower oil | — | 395.00 | — |
| Maize oil | — | — | 395.00 |
| Gelucire 50/13 | 55.00 | 55.00 | 55.00 |
| Total | 550.00 | 550.00 | 550.00 |

TABLE 23

Fill formulation trials with Gelucire 44/14

| Fill | I&D-0101-21 mg/cp | I&D-0102-21 mg/cp | I&D-0103-21 mg/cp |
|---|---|---|---|
| Iberogast N concentrate | 100.00 | 100.00 | 100.00 |
| Olive oil | 355.00 | — | — |
| Sunflower oil | — | 355.00 | — |
| Maize oil | — | — | 355.00 |
| Gelucire 44/14 | 95.00 | 95.00 | 95.00 |
| Total | 550.00 | 550.00 | 550.00 |

The methods to test the physicochemical parameters have been previously described.

Results

TABLE 24

Physicochemical parameters of the fill formulations with the hygroscopic fill tested

| Fill | I&D-0090-21 Result | I&D-0091-21 Result | I&D-0107-21 Result |
|---|---|---|---|
| Appearance | Homogeneous suspension | Homogeneous suspension | Homogeneous suspension |
| Fluidity at 30° C. (s) | Fill does not flow | 487 | 310 |
| Viscosity at 30° C. (cPs) | 4969 | 4079 | 3279 |
| Density at 30° C. (g/ml) | 1.14 | 1.14 | 1.14 |
| pH | 6.71 | 6.80 | 6.71 |
| Water (%) | 8.96 | 8.72 | 8.44 |
| $a_w$ | 0.4752 | 0.4670 | 0.4476 |
| Phase separation at 30° C. & 40° C. | No phase separation | No phase separation | No phase separation |

Based on the criteria established to select fill formulation for prototyping, the fill formulation corresponding with I&D-0107-21 is considered feasible for moving forward to the manufacture of a pilot batch.

Tables 25 and 26 show the physicochemical parameters of the fill formulations with Geleol mono and diglycerides NF tested. Based on the criteria established to select fill formulation for prototyping, the fill formulations corresponding with I&D-0108-21, I&D-0109-21 and I&D-0110-21 were considered feasible for moving forward to manufacture of a pilot batch.

TABLE 25

Physicochemical parameters of the fill formulations with Geleol mono and diglycerides NF (40 mg)

| Fill | I&D-0092-21 Result | I&D-0093-21 Result | I&D-0094-21 Result |
|---|---|---|---|
| Appearance | Homogeneous suspension | Homogeneous suspension | Homogeneous suspension |
| Fluidity at 30° C. (s) | Fill does not flow | Fill does not flow | Fill does not flow |
| Viscosity at 30° C. (cPs) | 4239 | 4029 | 4019. |
| Density at 30° C. (g/ml) | N.A. | N.A. | N.A. |
| pH | N.A. | N.A. | N.A. |
| Water (%) | N.A. | N.A. | N.A. |
| $a_w$ | N.A. | N.A. | N.A. |
| Phase separation at 30° C. & 40° C. | N.A. | N.A. | N.A. |

TABLE 26

Physicochemical parameters of the fill formulations with Geleol mono and diglycerides NF (30 mg)

| Fill | I&D-0108-21 Result | I&D-0109-21 Result | I&D-0110-21 Result |
|---|---|---|---|
| Appearance | Homogeneous suspension | Homogeneous suspension | Homogeneous suspension |
| Fluidity at 30° C. (s) | 192 | 175 | 238 |
| Viscosity at 30° C. (cPs) | 3359 | 3239 | 2959 |
| Density at 30° C. (g/ml) | 0.95 | 0.95 | 0.96 |
| pH | 5.20 | 5.21 | 5.22 |
| Water (%) | 7.94 | 7.79 | 7.51 |
| $a_w$ | 0.8129 | 0.8249 | 0.8154 |
| Phase separation at 30° C. & 40° C. | No phase separation | No phase separation | No phase separation |

Whilst in principle suitable, based on the criteria established to select the most preferred fill formulations for prototyping, the fill formulations corresponding with I&D-0095-21, I&D-0096-21, I&D-0097-21, I&D-0098-21, I&D-0099-21, I&D-0100-21, I&D-0101-21, I&D-0102-21 and I&D-0103-21 were considered less favourable and thus not chosen for moving forward to the manufacture of pilot batches.

CONCLUSIONS

Based on the insight stemming from the formulation trials, the following was concluded:

Fill compositions corresponding to the formulas I&D-0107-21, I&D-0108-21, I&D-0109-21 and I&D-0110-21 are over all the most formulations suitable to be encapsulated in soft gelatine capsules.

Fill composition corresponding to the formula I&D-0107-21, shows a higher value of water activity (0.45) than the fill corresponding to G2 (0.36), which exhibited brittleness. Higher value of water activity in the fill, means less migration phenomena during encapsulation and capsule storage.

Fill compositions of formulations, I&D-0108-21, I&D-0109-21 and I&D-0110-21 shows the highest value of water activity 0.81-0.82, being the value close to the wet shell water activity values (0.83 to 0.87), that means less migration phenomena during encapsulation. In addition, the hydrophobic characteristic of the fill may reduce the water intake from the shell during capsules shelf life.

Fill formulations proposed for pilot batches are outlined in table 27:

| Fill | I&D-0107-21 mg/cp | I&D-0108-21 mg/cp | I&D-0109-21 mg/cp | I&D-0110-21 mg/cp |
|---|---|---|---|---|
| Iberogast N concentrate | 100.00 | 100.00 | 100.00 | 100.00 |
| Macrogol 600 | 415.00 | — | — | — |
| Macrogol 4000 | 35.00 | — | — | — |
| Olive oil | — | 420.00 | — | — |
| Sunflower oil | — | — | 420.00 | — |
| Maize oil | — | — | — | 420.00 |
| Geleol mono and diglycerides | — | 30.00 | 30.00 | 30.00 |
| Total | 550.00 | 550.00 | 550.00 | 550.00 |

Two new prototypes were manufactured, pilot batch G9, corresponding to fill formulation I&D-0107-21 and pilot batch G11, corresponding to fill formulation I&D-108-21.

So far, capsules do not show brittleness at none of the chosen storage conditions, physical stability studies are currently ongoing.

TABLE 28

Physicochemical parameters of pilot batch G9:

| Parameter | Time 0 | 3 months 25° C.- 60% HR | 3 months 30° C.- 75% HR | 3 months 40° C.- 75% HR |
|---|---|---|---|---|
| Flexibility (N) | 7.2 | 12.3 | 12.0 | 7.4 |
| Fragility test (% of broken capsules) | 0% (n = 25) w = 100 g | 0% (n = 25) w = 100 g | 0% (n = 25) w = 100 g | 8% (n = 25) w = 100 g |
| Disintegration test (h:min:sg) (Disintegration media) | 0:06:34 (water) | 0:06:30 (water) | 0:06:42 (water) | Fail (gastric juice) |

TABLE 29

Physicochemical parameters of pilot batch G11:

| Parameter | Time 0 | 3 months 25° C.- 60% HR | 3 months 30° C.- 75% HR | 3 months 40° C.- 75% HR |
|---|---|---|---|---|
| Flexibility (N) | 4.6 | 2.6 | 1.9 | 1.4 |
| Fragility test (% of broken capsules) | 0% (n = 25) w = 100 g | 0% (n = 25) w = 100 g | 0% (n = 25) w = 100 g | 0% (n = 25) w = 100 g |
| Disintegration test (h:min:sg) (Disintegration media) | 0:05:57 (water) | 0:05:16 (water) | 0:05:37 (water) | 0:06:20 (water) |

Example 5: Veggie Shell Capsules

In order to provide vegan solutions a soft gel capsule without gelatine has been developed for the Iberogast N concentrate fill and shell formulations are disclosed in table 30:

| | E-G14 |
|---|---|
| Fill | mg/cp |
| Iberogast N concentrate | 95.44 |
| Olive oil | 414.56 |
| Beeswax | 40.00 |
| Total | 550.00 |
| Shell | % |
| Seagel CAP 203 | 35.00 |
| Glycerin | 25.00 |
| Iron oxide red | 0.35 |
| Iron oxide black | 0.12 |
| Purified water | 39.53 |
| Total | 100.00 |

So far, capsules do not show brittleness at none of the storage conditions, physical stability studies are currently ongoing.

TABLE 31

Physicochemical parameters of pilot batch 14:

| Parameter | Time 0 | 1 months 25° C.- 60% HR | 1 months 30° C.- 75% HR | 1 months 40° C.- 75% HR |
|---|---|---|---|---|
| Flexibility (N) | 2.4 | 2.8 | 2.8 | 2.6 |
| Fragility test (% of broken capsules) | 0% (n = 25) w = 100 g | 0% (n = 25) w = 100 g | 0% (n = 25) w = 100 g | 0% (n = 25) w = 100 g |
| Disintegration test (h:min:sg) (Disintegration media) | 0:11:00 (water) | 0:09:20 (water) | 0:08:15 (water) | 0:04:02 (water) |

Example 6: Soft Gel Capsules with Gelatin RXL R2

In order to improve the disintegration time for fill formulations containing PEG, a new pilot batch was manufactured, which composition comprises PEG base fill (G16). Gelita®RXL R2, which is specifically designed to avoid failures in disintegration tests was included. The formulation is disclosed in table 32:

| | E-G16 |
|---|---|
| Fill | mg/cp |
| Iberogast N concentrate | 95.44 |
| Macrogol 600 | 445.06 |
| Colloidal Silicone dioxide | 9.00 |
| Total | 549.50 |
| Shell | % |
| gelatine GELITA ® RXL R2 | 52.00 |
| Glycerin | 20.00 |
| Purified water | 28.00 |
| Total | 100.00 |

Capsules do not show brittleness at release, physical stability study is currently ongoing.

TABLE 33

Physicochemical parameters of pilot batch 16:

| Parameter | Time 0 |
|---|---|
| Flexibility (N) | 6.7 |
| Fragility test (% of broken capsules) | 0% (n = 25) w = 100 g |
| Disintegration test (h:min:sg) (Disintegration media) | 0:05:59 (water) |

Example 7: Alternative Formulation to Improve Capsules Behaviour Regarding Stickiness of Oily Formulation For oily formulation the shell has been optimized in order to avoid capsules stickiness, the level of gelatine is increased up to 46% as follows:

TABLE 34

Shell and fill composition of pilot batch G18

| | E-G18 |
|---|---|
| Fill | mg/cp |
| Iberogast N concentrate | 96.37 |
| Soya oil | 413.13 |
| Beeswax | 40.00 |
| Total | 549.50 |
| Shell | % |
| Gelatin RXL | 46.00 |
| Glycerin | 20.00 |
| Iron oxide red | 0.35 |
| Iron oxide black | 0.12 |
| Purified water | 33.53 |
| Total | 100.00 |

Example 8: Alternative Formulations to Improve Disintegration

Furthermore, the shell formulation will be further optimized in order to avoid crosslinking, which is the root cause of the failure during the disintegration tests of fill formulations comprising PEG (hydrophilic fill).

Tables 35 and 36 show fill and shell formulations to include sorbitol sorbitan solution in shell formulation of hydrophilic fill.

TABLE 35

Shell and fill composition of pilot batch E-G22

| | E-G22 |
|---|---|
| Fill | mg/cp |
| Iberogast N concentrate | 90* |
| Macrogol 600 | 451* |
| Colloidal Silicone dioxide | 9.00 |
| Total | 550.00 |
| Shell | % |
| Gelatin RXL | 43.50 |
| Glycerin | 10.00 |

TABLE 35-continued

| Shell and fill composition of pilot batch E-G22 | |
| --- | --- |
|  | E-G22 |
| Sorbitol sorbitan solution | 10.00 |
| Purified water | 36.50 |
| Total | 100.00 |

*Values to be defined considering the concentration of the Iberogast N concentrate

TABLE 36

| Shell and fill composition of pilot batch E-G23 | |
| --- | --- |
|  | E-G23 |
| Fill | mg/cp |
| Iberogast N concentrate | 90* |
| Macrogol 600 | 451* |
| Colloidal Silicone dioxide | 9.00 |
| Total | 550.00 |
| Shell | % |
| gelatine GELITA ® RXL R2 | 52.00 |
| Glycerin | 10.00 |
| Sorbitol sorbitan solution | 10.00 |
| Purified water | 28.00 |
| Total | 100.00 |

*Values to be defined considering the concentration of the Iberogast N concentrate

What is claimed is:

1. A pharmaceutical or dietary supplement composition in the form of a soft gel capsule, the capsule comprising a liquid or semisolid fill and a shell, wherein the fill comprises:
   a) at least one active ingredient or dietary supplement dissolved, suspended, or solubilized in a solution comprising less than 50% (w/w) of water and less than 5% (w/w) of alcohol wherein the active ingredient is a plant extract comprising a combination of Matricaria flower liquid extract, peppermint leaves liquid extract, liquorice root liquid extract, caraway fruit liquid extract, bitter candytuft fresh plant liquid extract, and Melissa leaf liquid extract;
   b) at least one solubilizer, wherein the solubilizer is selected from the group consisting of low molecular weight polyethylene glycol (PEG) having a molecular weight of 300 to 600 and plant oils selected from the group consisting of soybean oil, sunflower oil, olive oil, maize oil, and medium-chain triglycerides; and
   c) at least one thickening agent, wherein the thickening agent is selected from the group consisting of high molecular weight polyethylene glycol beeswax, glycerol monostearate 40-55, colloidal silicone dioxide, hard fat, lauroyl polyoxyl-32 glycerides, stearoyl macrogol-32 glycerides, and combinations thereof; and
wherein the shell comprises an edible polymer and optionally one or more of a plasticizer, an opacifier, and colorants.

2. The pharmaceutical or dietary supplement composition of claim 1, wherein the active ingredient is about 15% ethanolic extract of fresh plants of bitter candytuft, about 15% ethanolic extract of Melissa leaf, about 20% ethanolic extract of caraway fruit, about 10% ethanolic extract of liquorice root, about 30% ethanolic extract of Matricaria flower, and about 10% ethanolic extract of peppermint leaves.

3. The pharmaceutical or dietary supplement composition of claim 2, wherein the ethanolic extract of fresh plants of bitter candytuft is at a ratio of 1 part fresh plants of bitter candytuft to 1.5-2.5 parts of ethanol 50% (v/v), the ethanolic extract of Melissa leaf is at a ratio of 1 part Melissa leaf to 2.5-3.5 parts of ethanol 30% (v/v), the ethanolic extract of caraway fruit is at a ratio of 1 part caraway fruit to 2.5-3.5 parts of ethanol 30% (v/v), the ethanolic extract of liquorice root is at a ratio of 1 part liquorice root to 2.5-3.5 parts of ethanol 30% (v/v), the ethanolic extract of Matricaria flower is at a ratio of 1 part Matricaria flower to 2-4 parts of ethanol 30% (v/v), and the ethanolic extract of peppermint leaves is at a ratio of 1 part peppermint leaves to 2.5-3.5 parts of ethanol 30% (v/v).

4. The pharmaceutical or dietary supplement composition of claim 3, wherein the active ingredient comprises 15% of the ethanolic extract of fresh plants of bitter candytuft is at a ratio of 1 part fresh plants of bitter candytuft to 1.5-2.5 parts of ethanol 50% (v/v), 15% of the ethanolic extract of Melissa leaf is at a ratio of 1 part Melissa leaf to 2.5-3.5 parts of ethanol 30% (v/v), 20% of the ethanolic extract of caraway fruit is at a ratio of 1 part caraway fruit to 2.5-3.5 parts of ethanol 30% (v/v), 10% of the ethanolic extract of liquorice root is at a ratio of 1 part liquorice root to 2.5-3.5 parts of ethanol 30% (v/v), 30% of the ethanolic extract of Matricaria flower is at a ratio of 1 part Matricaria flower to 2-4 parts of ethanol 30% (v/v), and 10% of the ethanolic extract of peppermint leaves is at a ratio of 1 part peppermint leaves to 2.5-3.5 parts of ethanol 30% (v/v).

5. The pharmaceutical or dietary supplement composition of claim 1, wherein the solution comprising water and alcohol comprises:
   i. less than 5% (w/w), less than 4% (w/w), less than 3% (w/w), less than 2%, less than 1% (w/w), less than 0.5% (w/w), or less than 0.25% (w/w) of alcohol, wherein the alcohol is ethanol; and
   ii. less than 50% (w/w), less than 45% (w/w), less than 40% (w/w), less than 35% (w/w), less than 30% (w/w), less than 25% (w/w), less than 20% (w/w), or less than 15% (w/w) of water.

6. The pharmaceutical or dietary supplement composition of claim 1, wherein the solution comprising water and alcohol comprises
   i. between 5% to 0.2% (w/w), between 4% to 0.5% (w/w), between 3% to 1% (w/w), between 2% to 1% (w/w), between 2% to 0.5% (w/w), or between 1% to 0.2% (w/w) of alcohol wherein the alcohol is ethanol; and
   ii. between 10% to 50% (w/w), between 20% to 50% (w/w), between 30% to 50% (w/w), between 35% to 50% (w/w), between 40% to 50% (w/w), between 45% to 50% (w/w), between 15% to 49% (w/w), between 20% to 48% (w/w), between 25% to 47% (w/w), between 30% to 46% (w/w), or between 35% to 45% (w/w) of water.

7. The pharmaceutical or dietary supplement composition of claim 1, wherein
   a) the active ingredient is dissolved, suspended or solubilized in a solution comprising less than 2% (w/w) of alcohol, wherein the alcohol is ethanol, and less than 50% (w/w) of water;
   b) the at least one solubilizer is selected from the group consisting of polyethylene glycol 600, sunflower oil, olive oil, maize oil, and combinations thereof; and c) the at least one thickening agent is selected from polyethylene glycol 4000, glycerol monostearate 40-55 (Type I) EP/mono and diglycerides NF, colloidal silicone dioxide, beeswax, and combinations thereof; and wherein the shell comprises an edible polymer and optionally one or more of a plasticizer, an opacifier, and colorants.

8. The pharmaceutical or dietary supplement composition of claim 1, wherein the active ingredient is a hydrophilic plant extract.

9. The pharmaceutical or dietary supplement composition of claim 1, wherein the edible polymer is selected from the group consisting of gelatine, a blend of gelatine and low molecular weight gelatine hydrolysate, and a non-animal-derived compound, wherein said non-animal-derived compound is selected from the group consisting of, carrageenan, vegetable starch, and combinations thereof.

10. The pharmaceutical or dietary supplement composition of claim 1, wherein:
   a) the active ingredient comprises 15% of the ethanolic extract of fresh plants of bitter candytuft is at a ratio of 1 part fresh plants of bitter candytuft to 1.5-2.5 parts of ethanol 50% (v/v), 15% of the ethanolic extract of Melissa leaf is at a ratio of 1 part Melissa leaf to 2.5-3.5 parts of ethanol 30% (v/v), 20% of the ethanolic extract of caraway fruit is at a ratio of 1 part caraway fruit to 2.5-3.5 parts of ethanol 30% (v/v), 10% of the ethanolic extract of liquorice root is at a ratio of 1 part liquorice root to 2.5-3.5 parts of ethanol 30% (v/v), 30% of the ethanolic extract of Matricaria flower is at a ratio of 1 part Matricaria flower to 2-4 parts of ethanol 30% (v/v), and 10% of the ethanolic extract of peppermint leaves is at a ratio of 1 part peppermint leaves to 2.5-3.5 parts of ethanol 30% (v/v);
   b) the at least one solubilizer is selected from group consisting of polyethylene glycol 600, sunflower oil, olive oil, maize oil, and combinations thereof; c) the at least one thickening agent is selected from the group consisting of polyethylene glycol 4000, glycerol monostearate 40-55 (Type I) EP/mono and diglycerides NF, colloidal silicone dioxide, beeswax, and combinations thereof; and
   d) wherein the shell comprises an edible polymer selected from the group consisting of gelatine, a blend of gelatine and low molecular weight gelatine hydrolysate, and a non-animal-derived compound, wherein the non-animal-derived compound is selected from the group consisting of, carrageenan, vegetable starch, and combinations thereof.

11. The pharmaceutical or dietary supplement composition of claim 1, wherein the plasticizer is selected from the group consisting of glycerine, propylene glycol, mannitol, sorbitan, sorbitol, low molecular weight polyol, and combinations thereof.

12. The pharmaceutical or dietary supplement composition of claim 1, wherein the opacifier is selected from the group consisting of starch, titanium dioxide, calcium carbonate, zinc oxide, tricalcium phosphate, iron oxides, and combinations thereof.

13. The pharmaceutical or dietary supplement composition of claim 1, wherein:
   (i) a water activity value of the fill is between 0.30 and 0.60, between 0.35 and 0.50, between 0.37 and 0.47, or between 0.38 and 0.45; or
   (ii) the water activity value of the fill is between 0.70 and 0.90, between 0.73 and 0.85, between 0.74 and 0.84, or between 0.75 and 0.83.

14. A method of reducing brittleness of a soft gel capsule as claimed in claim 1, wherein a solubilizer is added to the fill before encapsulation with the shell, wherein the solubilizer is selected from group consisting of polyethylene glycol 400, polyethylene glycol 600, plant oils, and combinations thereof.

15. A method of reducing the fragility of pharmaceutical or dietary composition of claim 1, comprising adding a solubilizer to the fill before encapsulation with the shell, wherein the solubilizer is selected from polyethylene glycol 400, polyethylene glycol 600, plant oils, and combinations thereof.

16. A pharmaceutical or dietary supplement composition according to claim 1, for use in the treatment of functional disorders of the gastrointestinal (GI) tract, wherein the functional disorders of the GI tract is selected from the group consisting of functional dyspepsia (FD), irritable bowel syndrome (IBS), minor gastro-intestinal complaints, and functional impairments of the GI tract accompanying disease of the locomotor apparatus of rheumatic origin, wherein the accompanying disease is selected from the group consisting of rheumatoid arthritis, arthroses, spinal syndromes, epicondylitis, periarthritis, Bechterew's disease, and lumbago.

\* \* \* \* \*

UNITED STATES PATENT AND TRADEMARK OFFICE
CERTIFICATE OF CORRECTION

PATENT NO. : 11,793,761 B2
APPLICATION NO. : 18/122812
DATED : October 24, 2023
INVENTOR(S) : Barroso et al.

Page 1 of 2

It is certified that error appears in the above-identified patent and that said Letters Patent is hereby corrected as shown below:

In the Specification

In Column 3, Lines 1-2, delete "silicone" and insert -- silicon --, therefor.
In Column 3, Line 28, delete "25% 15" and insert -- 25% --, therefor.
In Column 3, Line 41, delete "silicone" and insert -- silicon --, therefor.
In Column 4, Line 26, delete "silicone" and insert -- silicon --, therefor.
In Column 5, Lines 54-55, delete "silicone" and insert -- silicon --, therefor.
In Column 6, Line 49, delete "silicone" and insert -- silicon --, therefor.
In Column 8, Line 8, delete "also these" and insert -- these --, therefor.
In Column 8, Line 16, delete "silicone" and insert -- silicon --, therefor.
In Column 9, Line 1, delete "silicone" and insert -- silicon --, therefor.
In Column 13, Line 7, delete "silicone" and insert -- silicon --, therefor.
In Column 13. Line 19, delete "silicone" and insert -- silicon --, therefor.
In Column 14. Line 32, delete "silicone," and insert -- silicon, --, therefor.
In Column 14, Line 40, delete "silicone," and insert -- silicon, --, therefor.
In Column 15, Lines 9-10, delete "polyethyelene" and insert -- polyethylene --, therefor.
In Column 21, Line 31, delete "Silicone" and insert -- Silicon --, therefor.
In Column 23, Line 24, delete "(mPa.$)." and insert -- (mPa.s). --, therefor.
In Column 23, Line 57, delete "024 to 036" and insert -- $C_{24}$ to $C_{36}$ --, therefor.
In Column 24, Line 13, delete "Silicone" and insert -- Silicon --, therefor.
In Column 26, Line 26, delete "Silicone" and insert -- Silicon --, therefor.
In Column 33, Line 55, delete "Silicone" and insert -- Silicon --, therefor.
In Column 34, Line 60, delete "Silicone" and insert -- Silicon --, therefor.
In Column 35, Line 21, delete "Silicone" and insert -- Silicon --, therefor.

In the Claims

In Column 35, Line 57, in Claim 1, delete "glycol" and insert -- glycol, --, therefor.
In Column 35, Line 58, in Claim 1, delete "silicone" and insert -- silicon --, therefor.
In Column 36, Line 21, in Claim 4, delete "is", therefor.

Signed and Sealed this
Fifteenth Day of July, 2025

Coke Morgan Stewart
*Acting Director of the United States Patent and Trademark Office*

CERTIFICATE OF CORRECTION (continued)
U.S. Pat. No. 11,793,761 B2

In Column 36, Line 24, in Claim 4, delete "is", therefor.
In Column 36, Line 26, in Claim 4, delete "is", therefor.
In Column 36, Line 28, in Claim 4, delete "is", therefor.
In Column 36, Line 30, in Claim 4, delete "is", therefor.
In Column 36, Line 32, in Claim 4, delete "is", therefor.
In Column 36, Line 38, in Claim 5, delete "2%," and insert -- 2% (w/w), --, therefor.
In Column 36, Line 47, in Claim 6, delete "comprises" and insert -- comprises: --, therefor.
In Column 36, Line 60, in Claim 7, delete "wherein" and insert -- wherein: --, therefor.
In Column 37, Lines 1-2, in Claim 7, after 'selected from' insert -- the group consisting of --, therefor.
In Column 37, Lines 3-4, in Claim 7, delete "silicone" and insert -- silicon --, therefor.
In Column 37, Lines 4-6, in Claim 7, delete ";and wherein the shell comprises an edible polymer and optionally one or more of a plasticizer, an opacifier, and colorants", therefor.
In Column 37, Line 20, in Claim 10, delete "is", therefor.
In Column 37, Line 23, in Claim 10, delete "is", therefor.
In Column 37, Line 25, in Claim 10, delete "is", therefor.
In Column 37, Line 27, in Claim 10, delete "is", therefor.
In Column 37, Line 29, in Claim 10, delete "is", therefor.
In Column 37, Line 32, in Claim 10, delete "is", therefor.
In Column 37, Line 34, in Claim 10, after 'selected from' insert -- the --, therefor.
In Column 37, Line 41, in Claim 10, delete "silicone" and insert -- silicon --, therefor.
In Column 38, Line 22, in Claim 14, delete "a" and insert -- the --, therefor.
In Column 38, Line 24, in Claim 14, after 'selected from' insert -- the --, therefor.
In Column 38, Line 28, in Claim 15, delete "a" and insert -- the --, therefor.
In Column 38, Line 30, in Claim 15, after 'selected from' insert -- the group consisting of --, therefor.